US011543725B2

(12) United States Patent
Zang

(10) Patent No.: US 11,543,725 B2
(45) Date of Patent: Jan. 3, 2023

(54) FLEXIBLE CONTROLLED-RELEASE FILM

(71) Applicant: E Ink California, LLC, Fremont, CA (US)

(72) Inventor: HongMei Zang, Fremont, CA (US)

(73) Assignee: E INK CALIFORNIA, LLC, Fremont, CA (US)

(*) Notice: Subject to any disclaimer, the term of this patent is extended or adjusted under 35 U.S.C. 154(b) by 72 days.

(21) Appl. No.: 16/422,508

(22) Filed: May 24, 2019

(65) Prior Publication Data
US 2019/0374759 A1 Dec. 12, 2019

Related U.S. Application Data

(63) Continuation of application No. 14/450,159, filed on Aug. 1, 2014, now abandoned, which is a continuation-in-part of application No. 13/426,464, filed on Mar. 21, 2012, now Pat. No. 8,830,561, which is a continuation-in-part of application No. 11/774,773, filed on Jul. 9, 2007, now abandoned.

(60) Provisional application No. 60/831,779, filed on Jul. 18, 2006.

(51) Int. Cl.
A61M 35/00 (2006.01)
G02F 1/167 (2019.01)
A45D 33/00 (2006.01)
C09K 19/54 (2006.01)
A61Q 19/00 (2006.01)
A61K 8/02 (2006.01)
A61K 8/81 (2006.01)
G02F 1/1681 (2019.01)

(52) U.S. Cl.
CPC ............ G02F 1/167 (2013.01); A45D 33/00 (2013.01); A61K 8/0208 (2013.01); A61K 8/8129 (2013.01); A61Q 19/00 (2013.01); C09K 19/544 (2013.01); C09K 2019/546 (2013.01); G02F 1/1681 (2019.01)

(58) Field of Classification Search
None
See application file for complete search history.

(56) References Cited

U.S. PATENT DOCUMENTS

| | | | |
|---|---|---|---|
| 4,126,854 A | 11/1978 | Sheridon | |
| 5,754,332 A | 5/1998 | Crowley | |
| 5,754,338 A | 5/1998 | Wilson et al. | |
| 5,762,823 A | 6/1998 | Hikmet | |
| 5,797,898 A | 8/1998 | Santini, Jr. et al. | |
| 6,020,175 A | 2/2000 | Onda et al. | |
| 6,037,008 A | 3/2000 | Huang et al. | |
| 6,294,620 B1 | 9/2001 | Huang et al. | |
| 6,497,942 B2 | 12/2002 | Sheridon et al. | |
| 6,565,532 B1 | 5/2003 | Yuzhakov et al. | |
| 6,588,131 B2 | 7/2003 | O'Connell, Jr. | |
| 6,795,138 B2 | 9/2004 | Liang et al. | |
| 6,795,229 B2 | 9/2004 | Liang et al. | |
| 6,821,455 B2 | 11/2004 | Kornfield et al. | |
| 6,859,302 B2 | 2/2005 | Liang et al. | |
| 6,885,495 B2 | 4/2005 | Liang et al. | |
| 6,912,038 B2 | 6/2005 | Liao et al. | |
| 6,930,818 B1 | 8/2005 | Liang et al. | |
| 6,947,202 B2 | 9/2005 | Liang et al. | |
| 6,982,181 B2 | 1/2006 | Hideo | |
| 7,005,468 B2 | 2/2006 | Zang et al. | |
| 7,095,477 B2 | 8/2006 | Liang et al. | |
| 7,141,279 B2 | 11/2006 | Liang et al. | |
| 7,158,282 B2 | 1/2007 | Liang et al. | |
| 7,245,414 B2 | 7/2007 | Liang et al. | |
| 7,259,744 B2 | 8/2007 | Arango et al. | |
| 7,261,920 B2 | 8/2007 | Haubrich et al. | |
| 7,401,758 B2 | 7/2008 | Liang et al. | |
| 7,408,696 B2 | 8/2008 | Liang et al. | |
| 7,488,230 B2 | 2/2009 | Ding et al. | |
| 7,560,004 B2 | 7/2009 | Pereira et al. | |
| 7,658,864 B2 | 2/2010 | Yoshikawa et al. | |
| 7,716,946 B2 * | 5/2010 | Fralick .................. | F25B 43/006 62/471 |
| 7,754,338 B2 | 7/2010 | Anderson | |
| 7,875,107 B2 | 1/2011 | Mori et al. | |
| 8,263,060 B2 | 9/2012 | Uhrich et al. | |
| 8,282,762 B2 | 10/2012 | Liang | |

(Continued)

FOREIGN PATENT DOCUMENTS

JP H0417990 A 1/1992
JP H04179918 A 6/1992

(Continued)

OTHER PUBLICATIONS

Liang, R.C., "BreakThrough-Newly-Developed Color Electronic Paper Promises—Unbeatable Production Efficiency", Nikkei Microdevices, p. 3 (Dec. 2002). (in Japanese, with English translation). Dec. 1, 2002.

Liang, R.C. et al., "Microcup Electrophoretic Displays by Roll-to-Roll Manufacturing Processes", IDW '02, Paper EP2-2, pp. 1337-1340, (Dec. 2002). Dec. 4, 2002.

Liang, R.C., "Microcup Electrophoretic and Liquid Crystal Displays by Roll-to-Roll Manufacturing Processes", Presented at Flexible Microelectronics & Displays Conference of U.S. Display Consortium, Phoenix, Arizona, USA (Feb. 2003). Feb. 3, 2003.

Liang, R.C. et al., "Microcup LCD, A New Type of Dispersed LCD by a Roll-to-Roll Manufacturing Process", Presented at IDMC, Paper We-02-04, pp. 1-4, Taipei, Taiwan, (Feb. 2003). Feb. 18, 2003.

(Continued)

Primary Examiner — David J Blanchard
Assistant Examiner — Daniel F Coughlin
(74) Attorney, Agent, or Firm — Brian D. Bean

(57) ABSTRACT

The present invention is directed to a flexible controlled release film for delivering a medicinal or cosmetic agent, e.g., through the skin of a subject, which delivery system comprises (a) a microembossed flexible film including microcells; (b) a liquid composition filled in the microcells wherein said liquid composition comprises the medicinal or cosmetic agent; and (c) a flexible sealing layer to enclose the liquid composition within the microcells.

8 Claims, 13 Drawing Sheets

(56) References Cited

U.S. PATENT DOCUMENTS

| | | |
|---|---|---|
| 8,830,561 B2 | 9/2014 | Zang et al. |
| 2003/0203101 A1 | 10/2003 | Haubrich et al. |
| 2004/0039343 A1* | 2/2004 | Eppstein ............... A61N 1/325 604/200 |
| 2004/0120024 A1 | 6/2004 | Chen et al. |
| 2004/0219306 A1 | 11/2004 | Wang et al. |
| 2004/0253299 A1* | 12/2004 | Beier .................. A61K 9/7084 424/449 |
| 2007/0059351 A1* | 3/2007 | Murrell ............... A61K 9/7061 424/449 |
| 2007/0078414 A1 | 4/2007 | McAllister et al. |
| 2008/0020007 A1 | 1/2008 | Zang |

FOREIGN PATENT DOCUMENTS

| | | |
|---|---|---|
| JP | 2004179918 A | 6/2004 |
| JP | 2005308854 A | 11/2005 |
| JP | 2007168148 A | 7/2007 |

OTHER PUBLICATIONS

Liang, R.C. et al., "Passive Matrix Microcup Electrophoretic Displays", IDMC'03, Paper FR-17-5, p. 1-4, Taipei, Taiwan, (Feb. 2003). Feb. 18, 2003.

Liang, R.C. et al., "Microcup Displays: Electronic Paper by Roll-to-Roll Manufacturing Processes" Journal of the SID, 11 (4), pp. 621-628, (Feb. 2003). Feb. 18, 2003.

Chen, S.M., "Revolution electronic paper: The New Application and the Dynamics of Companies", Topology Research Institute, pp. 1-10, (May 2003). (In Chinese, English abstract attached) May 1, 2003.

Liang, R.C. et al., "Microcup Active and Passive Matrix Electrophoretic Displays by a Roll-to-Roll Manufacturing Processes", SID 03 Digest, Paper 20.1, pp. 838-841 (May 2003). May 21, 2003.

Lee, H. et al., "SiPix Microcup Electronic Paper—An Introduction" Advanced Display, Issue 37, pp. 4-9, (Jun. 2003). (in Chinese, English abstract attached) Jun. 1, 2003.

Chen, S.M., "The Applications for the Revolutionary Electronic Paper Technology", OPTO News & Letters, Issue 102, pp. 37-41 (Jul. 2003). (in Chinese, English abstract attached) Jul. 1, 2003.

Zang, H.M. et al., "Microcup Electronic Paper by Roll-to-Roll Manufacturing Processes", The Spectrum, 16(2), pp. 16-21 (2003). Jul. 1, 2003.

Allen, Kimberly, PhD., "Electrophoretics Fulfilled. Emerging Displays Review: Emerging Display Technologies, Monthly Report", Stanford Resources Display Insight, pp. 9-14, (Oct. 2003). Oct. 1, 2003.

Kleper, M. et al., "An Investigation of the Emerging and Developing Technologies Related to the Generation Beyond Print-on-Paper", Advanced Display Technologies, Rochester Institute of Technology, pp. 13-15, (Oct. 2003). Oct. 1, 2003.

Zang, H.M., "Microcup Electronic Paper by Roll-to-Roll Manufacturing Processes", Presentation at the Advisory Board Meeting, Bowling Green State Univ., Ohio, USA (Oct. 2003) Oct. 23, 2003.

Chung, J. et al., "Microcup Electrophoretic Displays, Grayscale and Color Rendition", IDW, AMD2 & EP1-2, pp. 243-246 (Dec. 2003). Dec. 1, 2003.

Ho, C. et al., "Microcup Electronic Paper by Roll-to-Roll Manufacturing Processes", Presentation conducted at FEG, Nei-Li, Taiwan, (Dec. 2003). Dec. 23, 2003.

Zang, H.M. et al., "Threshold and Grayscale Stability of Microcup Electronic Paper", SPIE vol. 5289, pp. 102-108, (Jan. 2004). Jan. 19, 2004.

Zang, H.M., "Microcup Electronic Paper", Presentation at the Displays & Microelectronics Conference of U.S. Display Consortium, Phoenix, Arizona, USA (Feb. 2004). Feb. 10, 2004.

Wang, X. et al., "Microcup Electronic Paper and the Converting Processes", ASID, 10.1.2-26, pp. 396-399, Nanjing, China, (Feb. 2004). Feb. 15, 2004.

Chaug, Y.S. et al., "Roll-to-Roll Processes for the Manufacturing of Patterned Conductive Electrodes on Flexible Subsirales", Mat. Res. Soc. Symp. Proc., vol. 814, 19.6.1., (Apr. 2004). Apr. 12, 2004.

Liang, R.C., "Microcup Electronic Paper by Roll-to-Roll Manufacturing Process", Presented at the Flexible Displays & Electronics 2004 of Intertech, San Fransisco, California, USA, (Apr. 2004). Apr. 28, 2004.

Hou, J. et al., "Reliability and Performance of Flexible Electrophoretic Displays by Roll-to-Roll Manufacturing Processes", SID Digest, 32.3, pp. 1066-1069 (May 2004). May 27, 2004.

Wang, X. et al., "Microcup Electronic Paper and the Converting Processes", Advanced Display, Issue 43, pp. 48-51 (Jun. 2004). (in Chinese, with English abstract) Jun. 1, 2004.

Liang, R.C. et al., "Format Flexible Microcup Electronic Paper by Roll-to-Roll Manufacturing Process", Presented at 14th FPD Manufacturing Technology Expo & Conference, Tokyo, Japan, (Jun. 30, 2004-Jul. 2, 2004). Jul. 2, 2004.

Liang, R.C., "Flexible and Rollable Displays/Electronic Paper—A Technology Overview", Presented at the METS Conference, Taipei, Taiwan, (Oct. 2004). Oct. 22, 2004.

Bardsley, J.N. et al., "Microcup Electrophoretic Displays", USDC Flexible Display Report, 3.1.2., pp. 3-12 to 3-16, (Nov. 2004). Nov. 1, 2004.

Ho, Candice, "Microcup Electronic Paper Device and Application", Presentation conducted at USDC 4th Annual Flexible Display and Microelectronics Conference, Phoenix, Arizona, USA, (Feb. 1, 2005). Feb. 1, 2005.

Zang, H.M. et al., "Flexible Microcup EPD by RTR Process", Presentation conducted at 2nd Annual Paper-Like Displays Conference, St. Pete Beach, Florida, USA, (Feb. 9-11, 2005). Feb. 10, 2005.

Liang, R.C., "Flexible and Roll-able Displays/Electronic Paper—A Brief Technology Overview", Presentation at Flexible Display Forum, Taiwan (Feb. 2005). Feb. 17, 2005.

Wang, X. et al., "Inkjet Fabrication of Multi-Color Microcup Electrophorectic Display", 5th Flexible Microelectronics & Displays Conference of U.S. Display Consortium, Phoenix, AZ, USA, (Feb. 2006). Feb. 9, 2006.

Zang, H.M., et al., "Monochrome and Area Color Microcup EPDs by Roll-to-Roll Manufacturing Processes", ICIS 06 International Congress of Imaging Science Final Program and Proceedings, pp. 362-365, Rochester, New York, USA (May 2006). May 9, 2006.

Wang, X. et al., "Roll-to-Roll Manufacturing Process for Full Color Electrophoretic Film", SID 06 Digest, vol. 37, Issue 1, pp. 1587-1589, (Jun. 2006) Jun. 8, 2006.

Zang, H.M., "Monochrome and Area Color Microcup EPDs by Roll-to-Roll Manufacturing Process", Presentation conducted at the Fourth Organic Electronics Conference and Exhibition (OEC-06), Frankfurt, Germany, (Sep. 25-27, 2006). Sep. 26, 2006.

Ho, Andrew, "Embedding e-Paper in Smart Cards, Pricing Labels & Indicators", Presentation conducted at Smart Paper Conference, Atlanta, GA, USA (Nov. 15-16, 2006). Nov. 15, 2006.

Zang, H.M., "Developments in Microcup Flexible Displays", Presentation conducted at the 6th Annual Flexible Display and Microelectronics Conference, Phoenix, AZ, Feb. 6-8, 2007. Feb. 7, 2007.

Zang, H.M. et al., "Microcup e-Paperfor Embedded and Flexible Designs", IDMC'07, Taipei International Convention Center, Taiwan, (Jul. 2007). Jul. 6, 2007.

Sprague, R.A., "SiPix Microcup Electrophoretic Epaper for Ebooks", NIP 25, 2009, pp. 460-462; (Sep. 23, 2009). Presentation conducted on Sep. 23, 2009 at the 25th Int'l Conference on Digital Printing Technologies,Louisville, Kentucky, USA.) Sep. 23, 2009.

Uhrich, Kathryn E. et al., "Synthesis and Characterization of Degradable Poly(anhydride-co-imides)", Macromolecules, vol. 28, pp. 2184-2193 (1995). Jan. 6, 1995.

\* cited by examiner

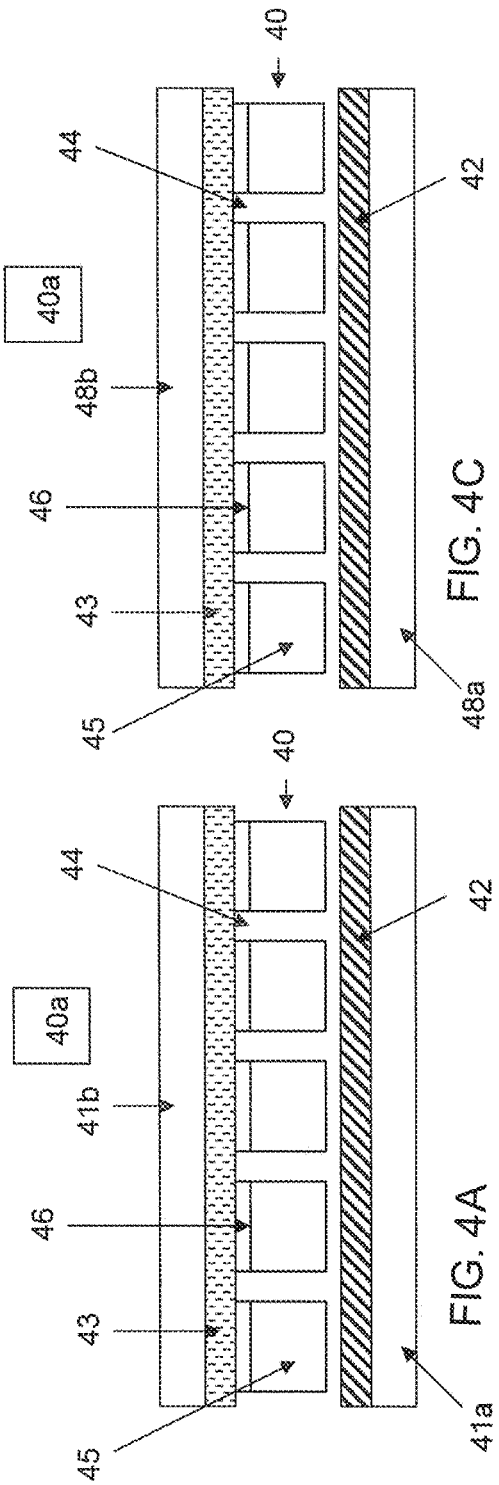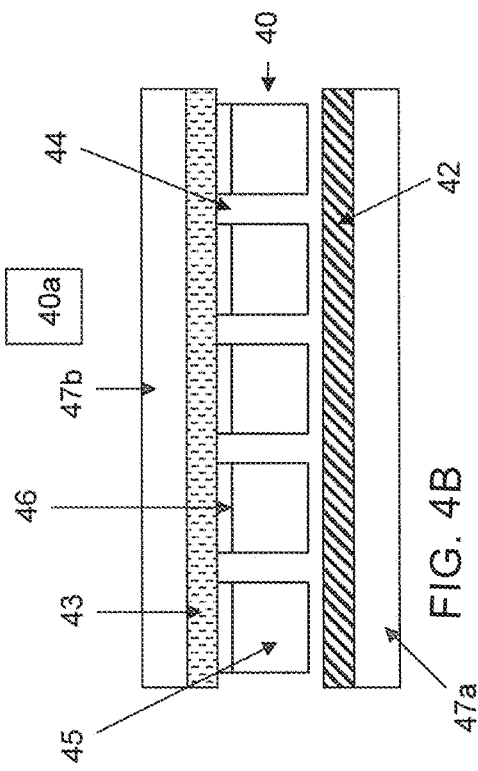

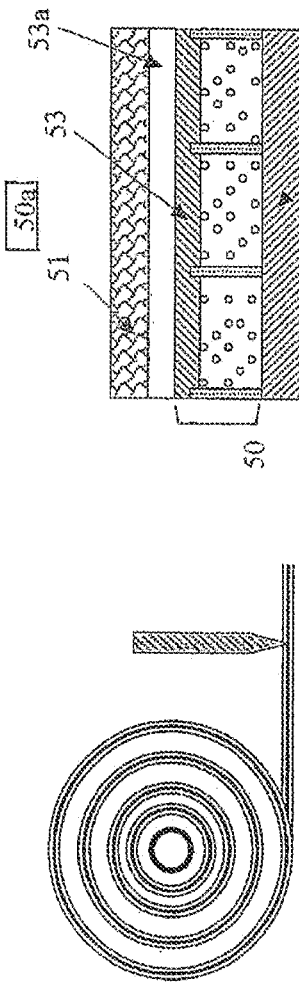
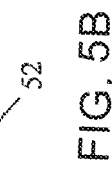
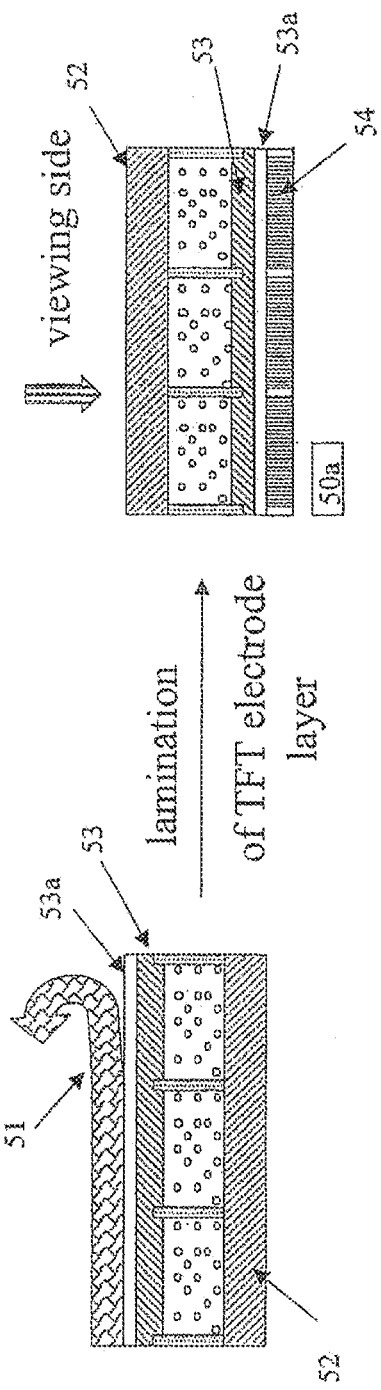
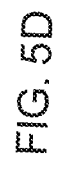

FLEXIBLE CONTROLLED-RELEASE FILM

This application is a continuation of U.S. application Ser. No. 14/450,159, filed Aug. 1, 2014, which is a continuation-in-part of U.S. application Ser. No. 13/426,464, filed Mar. 21, 2012, now U.S. Pat. No. 8,830,561; which is a continuation-in-part of U.S. application Ser. No. 11/774,773, filed Jul. 9, 2007, which claims the benefit of U.S. Provisional Application No. 60/831,779, filed Jul. 18, 2006. All applications and publications cited herein are incorporated by reference in their entireties.

BACKGROUND OF THE INVENTION

Various structures with peripheral plates or walls containing a liquid component were previously known. For example, a liquid component may be filled between two parallel or near-parallel surfaces and, in such a case, the liquid component is present in a continuous form. The two plates may be edge sealed first with fill holes for subsequent filling of the liquid component. Alternatively, the liquid component may be dropped on one of the two plates (before or after application of the edge sealing adhesive), followed by placing a second plate on top of the first plate to contain the liquid component between the two plates. In some cases, spacers may be present in the continuous liquid phase to control the distance between the two plates. However, such a continuous liquid phase structure suffers certain disadvantages. For example, it lacks structure integrity and depth control, especially when the plates are flexible substrates. In addition, this type of structure is not format flexible for production and, if hard surface plates are involved, batch manufacturing is required which results in low production efficiency.

It is also possible to divide a liquid component into small compartments, for example, by microencapsulation. Individual droplets are wrapped by a wall material to form discreet compartments and such compartments are arranged between two parallel or near-parallel surfaces. There are numerous examples of microencapsulation of a liquid component for different types of applications. In the display field, for example, there are encapsulated electrophoretic displays and encapsulated cholesterolic liquid crystal displays. In the pharmaceutical field, drugs may be encapsulated for controlled release. In the imaging field, dye and UV curable monomers may be encapsulated for light/pressure induced imaging development. In this approach, the performance of an encapsulated product or device often depends on the size distribution of the microcapsules. It could be challenging to control the size of the microcapsules to be within a desired range. In addition, the capsule wall usually does not provide good mechanical support for structural integrity, especially with flexible substrates. Material selection is another issue with the microencapsulation technique. In many cases, extra chemical(s) are necessary to stabilize the dispersed phase; the extra chemical(s), however, could be detrimental to the final product.

U.S. Pat. No. 6,930,818 and related patents and patent applications describe a microcup structure for monochrome or multi-color electrophoretic displays. An electrophoretic display device is formed when the microcups are filled with an electrophoretic fluid comprising charged pigment particles dispersed in a dielectric solvent or solvent mixture. U.S. Pat. No. 6,795,138 and related patents and patent applications disclose a liquid crystal display, also utilizing the microcup structure. The liquid crystal composition filled in the microcups may further comprise one or more guest dye(s), in particular, dichroic dye(s). US Patent Application Publication No. 2005-0012881A describes a display device which can display a 3-dimensional image and such a display device is formed when the microcups are filled with an optically active electrophoretic dispersion. US Patent Application Publication No. 2006-0139724 discloses an electrodeposition or electrochromic display device which is formed when the microcups are filled with an electrolyte fluid or an electrochromic fluid. The contents of all of the patents and patent applications referred to above are incorporated herein by reference in their entirety.

BRIEF DESCRIPTION OF THE DRAWINGS

FIGS. 4A-4C show the structures of display devices prepared from the film structure of the present invention.

FIGS. 5A-5D show how a semi-finished display panel may be converted to a finished display panel.

SUMMARY OF THE INVENTION

Figure 1:
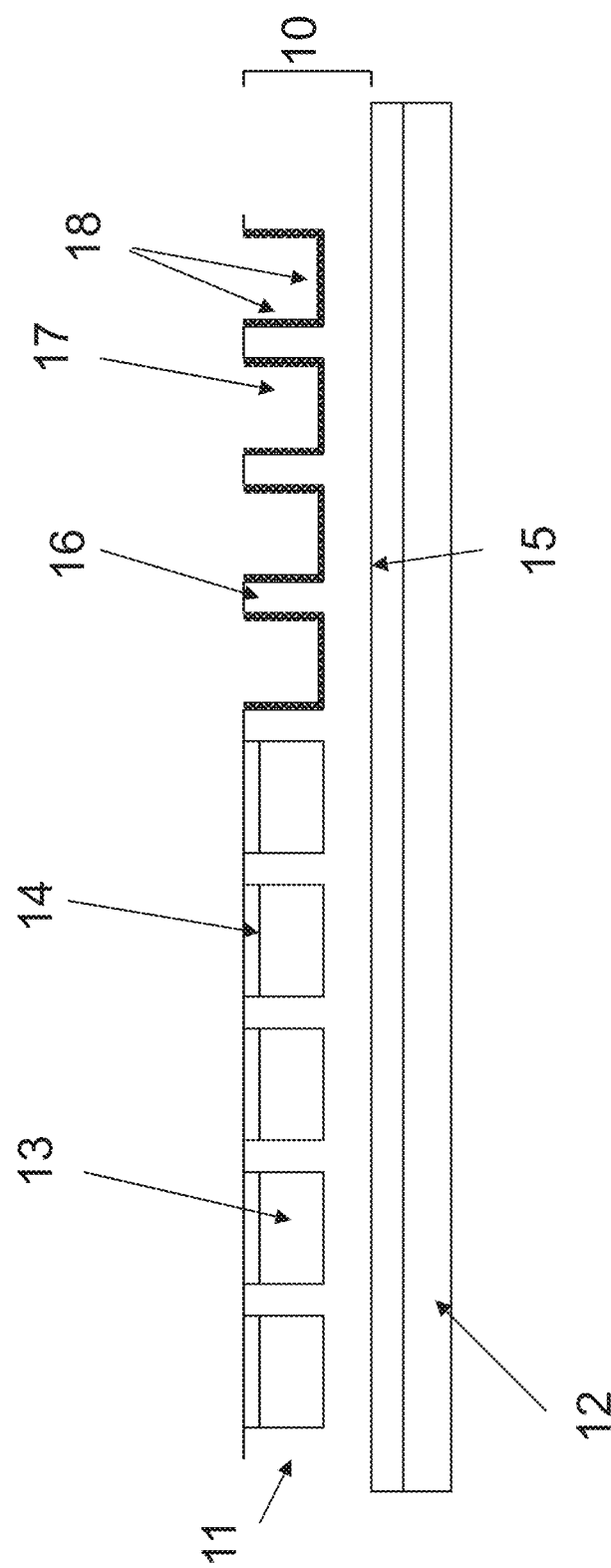
FIG. 1 illustrates a film structure of the present invention.

The present application describes a film structure which comprises one or more microcups and the microcups are filled with a liquid composition and top-sealed with a sealing layer which is hardened in situ.

The first aspect of the present invention is directed to a liquid crystal display, utilizing the film structure. The liquid crystal display comprises (a) one or more microcups comprising partition walls and top-openings, (b) a liquid crystal composition filled in the microcups which liquid crystal composition comprises liquid crystals and a polymer matrix or a three-dimensional polymer network; and (c) a sealing layer to enclose the liquid crystal composition within the microcups which sealing layer is hardened in situ. The liquid crystal composition is formed by hardening a precursor composition comprising liquid crystals and a polymer precursor. The precursor composition may be hardened before or after hardening of the sealing layer, or simultaneously when the sealing layer is being hardened.

Alternatively, the liquid crystal composition in the liquid crystal display may comprise liquid crystals, a chiral material and optionally a polymer network.

In another embodiment of the present invention, a display device may be prepared by (1) forming a film structure comprising microcups on a substrate, (2) forming a first conductive layer on the inside surface of the microcups including the side surface and bottom surface of the microcups and the top surface of the partition walls, (3) filling the microcups with a display fluid and sealing the filled microcups, and (4) laminating or depositing a second conductive layer onto the filled and sealed microcups, optionally with an adhesive layer. If the second conductive layer is deposited by, for example, printing, thin film sputtering or vapor deposition, a second substrate layer may be laminated onto the second conductive layer, optionally with an adhesive layer. In this embodiment, the first conductive layer is placed between the microcup surface and the display fluid. Optionally, an electrode protective layer, a textured layer, an alignment layer, an anchoring layer, or other performance enhancement layers may be coated onto the first conductive layer before the filling and sealing of the display fluid. Any of the display fluids disclosed in this application may be used in this embodiment of the invention.

The second aspect of the present invention is directed to a transdermal delivery system, utilizing the film structure. The transdermal delivery system comprises (a) one or more microcups comprising partition walls and top-openings; (b) a liquid composition filled in the microcups which liquid composition comprises a medicinal or cosmetic agent; and (c) a sealing layer to enclose the liquid composition within the microcups which sealing layer is hardened in situ. The microcups in the transdermal delivery system may be filled with liquid compositions containing different medicinal or cosmetic agents.

Using the film structure, a liquid composition is filled into individual microcups and the filled microcups are top-sealed. The size of the microcups can be predetermined and controlled. In addition, the microcup wall is in fact a built-in spacer to keep the top and bottom substrates apart at a fixed distance. The mechanical properties and structural integrity of the film structure are significantly improved. Furthermore, the use of the film structure eliminates the need of an edge seal adhesive required in the formation of a display panel. More importantly, the microcup-based film structure enables a format flexible manufacturing process wherein the process produces a continuous output of the film structure in a large sheet format which can be cut into any desired sizes afterwards.

DETAILED DESCRIPTION OF THE INVENTION

I. Film Structure

FIG. 1 illustrates the film structure (10), an electrophoretic display, which comprises one or more microcups (11). The microcups comprise partition walls (16) and top openings (17). The film structure (10) may be formed on a substrate layer (12) which may optionally comprise an electrode layer (not shown). There may also be an optional primer layer (15) between the microcups and the substrate layer (12). The microcups are filled with a liquid composition (13) and top-sealed with a polymeric sealing layer (14).

1. Formation of the Microcups (a) Microembossing

Figure 2A:
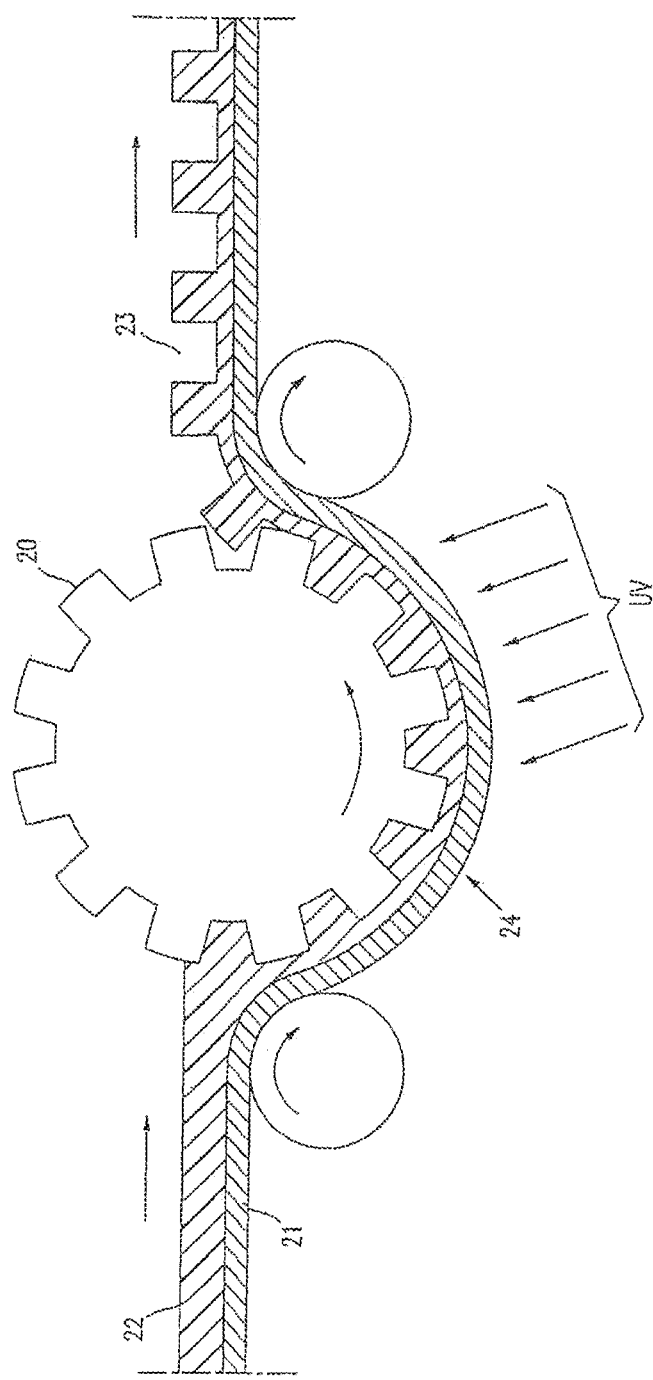
FIGS. 2A and 2B illustrate microembossing processes.
Figure 2B:
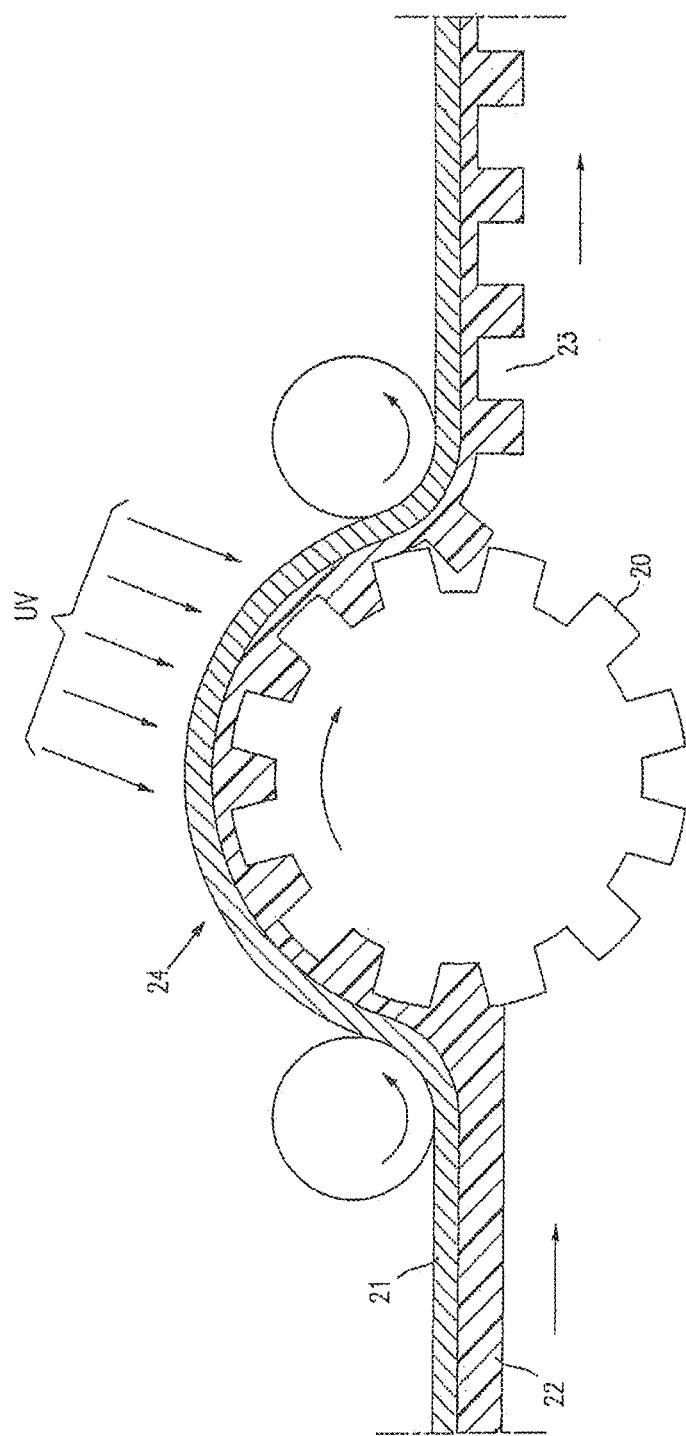

This processing step is shown in FIGS. 2A and 2B. A male mold (20) may be placed either above (FIG. 2A) or below (FIG. 2B) the web (24). The microcups may be formed on a flexible substrate layer (21). The substrate layer (21) may optionally comprise an electrode layer (not shown), which is suitable especially for display applications or other applications the operation of which involves the application of a voltage or current. The electrode layer, if present, usually is a transparent conductor film on the substrate layer. Alternatively, the substrate layer may be rigid and in such a case, the microcup layer may be fabricated by batch processes.

A layer of an embossable composition (22), such as a thermoplastic or thermoset precursor, is coated on the substrate layer (21). The embossable composition is embossed by the male mold (20) in the form of a roller, plate or belt, at a temperature higher than the glass transition temperature (or $T_g$) of the embossable composition.

Hard embossing may also be used. Conventional isothermal embossing technique comprises the steps of heating both a mold and a substrate to a temperature above the glass transition temperature ($T_g$) of the substrate. In this process, the top surface of the substrate is heated before embossing by passing it through an oven, an IR heater and/or hot rollers. If a non-isothermal embossing process is used, the process involves heating only the mold to a temperature higher than the $T_g$ of a top surface to be embossed. Embossing can be done directly on the top surface of a web (e.g., a thermoplastic web) or on the top surface of a thermoplastic polymer layer applied onto a web. In either case, the web has to be cooled before releasing from the mold to maintain a good embossing structure.

The embossable composition may be a multifunctional acrylate or methacrylate, vinylether, epoxide, an oligomer or polymer thereof or the like. Multifunctional acrylate and its oligomers are the most preferred. A combination of a multifunctional epoxide and a multifunctional acrylate is also very useful to achieve desirable physico-mechanical properties. A crosslinkable oligomer imparting flexibility, such as urethane acrylate or polyester acrylate, may also be added to improve the flexure resistance of the microcups formed. The embossable composition may further contain an oligomer, monomer, additives and optionally a polymer. The glass transition temperatures for this class of materials usually range from about −70° C. to about 150° C., preferably from about −20° C. to about 50° C. The microembossing process is typically carried out at a temperature higher than the $T_g$. A heated male mold or a heated housing substrate against which the mold presses may be used to control the microembossing temperature and pressure.

As shown in FIGS. 2A and 2B, the mold is released during or after the embossable composition is hardened to reveal the microcups (23). The hardening of the embossable composition may be accomplished by cooling, cross-linking by radiation, heat or moisture. If the curing of the embossable composition is accomplished by UV radiation, UV may radiate onto the substrate layer (21) which must be transparent from the bottom or the top of the web as shown in the two figures. Alternatively, UV lamps may be placed inside the mold. In this case, the mold must be transparent to allow the UV light to radiate through the mold onto the embossable composition.

Optionally, the microcup surface (i.e., the inside surface of the microcups in direct contact with the liquid composition) may be further modified after or during the microembossing process in order for a display device to achieve optimal performance. For example, for a LCD display device, an alignment layer or anchoring layer may be fabricated on the microcup surface. Polyimide, polyvinyl alcohol, polyamide, silicon dioxide, nylon, lecithin or a photoalignment material may be coated onto the microcup surface after microembossing, which may be accompanied by subsequent rubbing or photo exposure. In another scenario, the surface of the microcups may be textured which could be achieved by forming ordered micro-structures (for example, micro-groove structures with controlled incline angles) on the surface of the male mold. The micro-structures may be initially created on a photoresist layer during the LIGA (i.e., lithography, electroforming and molding) process for the mold fabrication, or engraved onto the male mold by diamond turn after the electroforming step. Through embossing, the micro-structures on the male mold will be transferred to the microcup surface. Such microstructures may be used to enhance the anchoring or control of the alignment and the pretilt angle of the liquid crystals. As a result, the performance of the liquid crystal display device is enhanced.

Within the microcups, there may be vertical protruding sub relief structures (e.g., acting as spacers) arising from the bottom of the microcups. The sub relief structures may be discrete structures such as columns, cylinders, wedges, crosses or continuous structures such as walls and grids. The top surface of the continuous sub structures may be of any shape and is preferred to be no larger than the bottom of the structures. The cross-section of the sub relief structures can be of any shapes, including round, square, rectangle, oval and others. Such sub relief structures may be prepared by microembossing or photolithography. Details of this feature are described in U.S. Pat. No. 6,947,202, the content of which is incorporated herein by reference in its entirety. The sub relief structures may be of the same height or lower than the microcup walls.

One of the examples for the preparation of the male mold is given in U.S. Pat. No. 6,930,818.

(b) Imagewise Exposure

Alternatively, the microcups may be prepared by imagewise exposure (FIGS. 3A-3B) of a radiation curable material (31) coated on a substrate layer (33) which may be flexible or rigid, to UV or other forms of radiation through a photomask (30). The substrate layer (33) may also comprise an electrode layer (32), depending on the application of the final device formed. In other words, electrode layer (32) in the figure may or may not be present. The electrode layer (32) may be present if the operation of the intended final product involves the application of a voltage or current, such as a display device. The electrode layer, if present, is a conductor film on the substrate layer.

For a roll-to-roll process, the photomask may be synchronized with the web and move at the same speed as the latter. In the photomask (30) in FIG. 3A, the dark squares (34) represent the opaque area and the space (35) between the dark squares represents the opening area. The UV radiates through the opening area (35) onto the radiation curable material (31). The exposed areas become hardened and the unexposed areas (protected by the opaque area in the mask) are then removed by an appropriate solvent or developer to form the microcups (36). The solvent or developer is selected from those commonly used for dissolving or reducing viscosity of radiation curable materials, such as methylethylketone, toluene, acetone, isopropanol or the like.

Figure 3A:
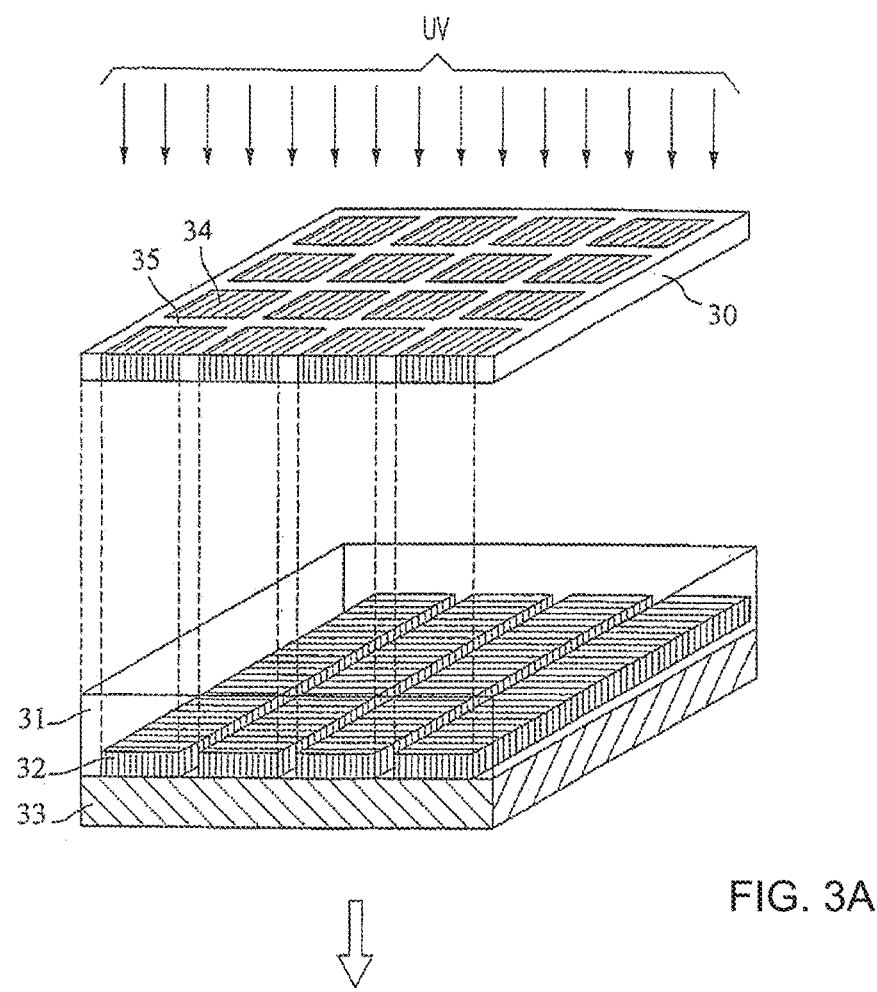
FIGS. 3A-3F illustrate the imagewise exposure processes for the preparation of microcups.
Figure 3B:
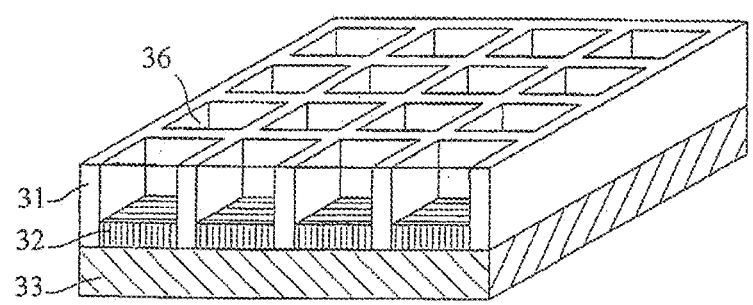

FIGS. 3C-3D and 3E-3F illustrate two other options for the preparation of microcups by imagewise exposure. The features in these two figures are essentially the same as shown in FIGS. 3A-3B and the corresponding parts are also numbered the same.

Figure 3D:
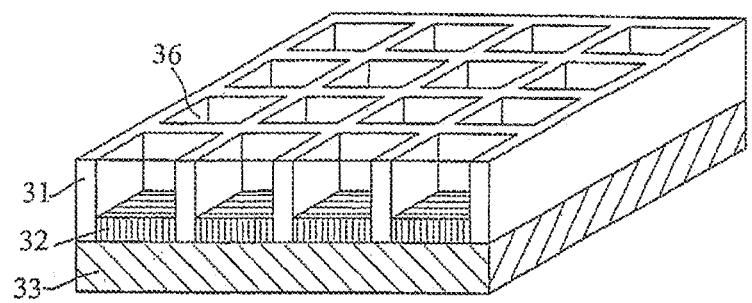
Figure 3C:
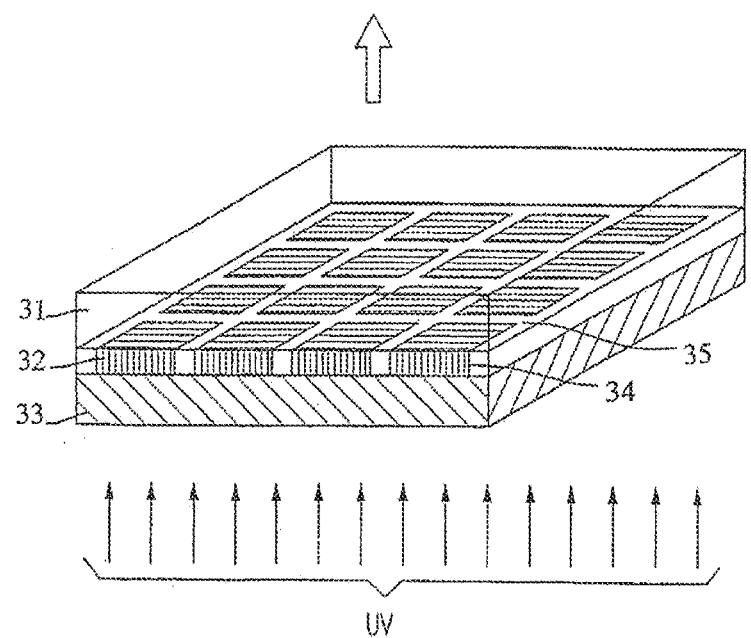

In FIGS. 3C-3D, the substrate (33) is opaque and pre-patterned. The electrode layer (32) is optionally present. In this case, the substrate layer (and the electrode layer if present) serves as a photomask. The microcups (36) can then be formed by removing the unexposed areas after UV radiation.

Figure 3F:
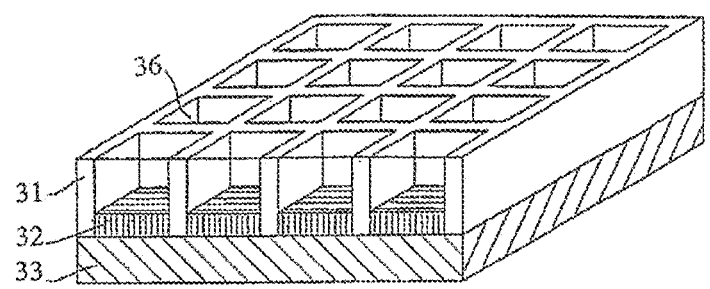
Figure 3E:
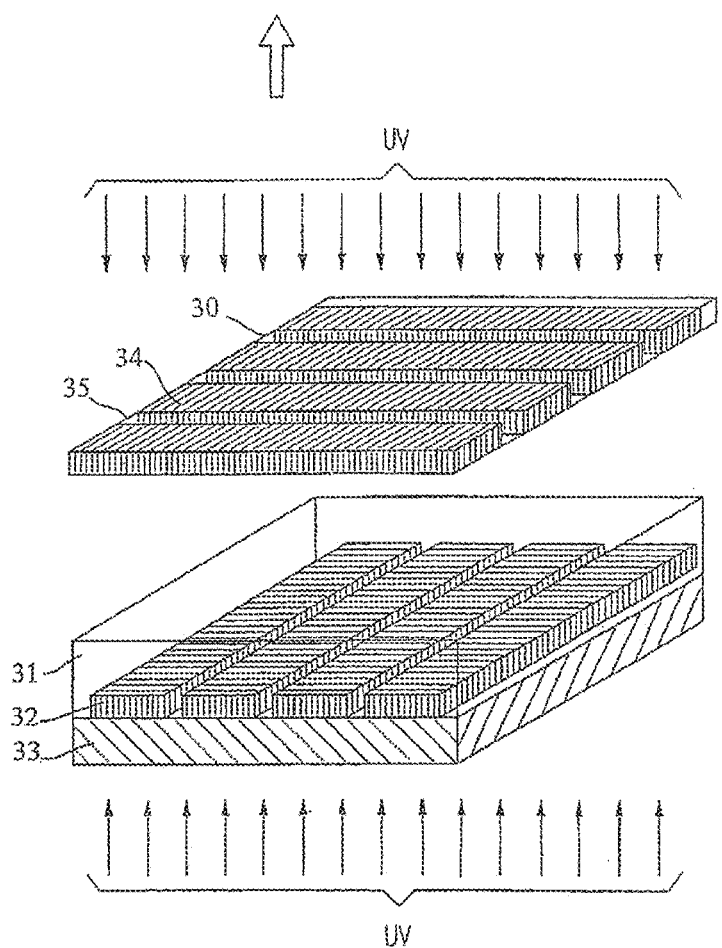

In FIGS. 3E-3F, the substrate layer (33) is also opaque and pre-patterned. The radiation curable material is exposed from the bottom through a line-pattern on the substrate layer (33) (and the electrode layer 32 if present) which also serves as the first photomask. A second exposure is performed from the other side through the second photomask (30) having a line pattern perpendicular to the first set of lines. The unexposed area is then removed by a solvent or developer to reveal the microcups (36).

(c) Pre-Punched Holes

The microcups may also be prepared by laminating a spacer film with an array of prepunched holes onto a substrate layer. Suitable spacer film materials for having prepunched holes may include thermoset or thermoplastic resins such as polyethylene terephthalate (PET), polyethylene naphthalate (PEN), polycarbonate, polymethyl methacrylate (PMMA), polysulfone, polystyrene, polyurethane, polysiloxanes, epoxy resins, polyolefins, polycycloolefins, polyamides, polyimides, cured vinyl esters, cured unsaturated polyesters, cured multifunctional vinyl ethers, cured multifunctional acrylates, cured multifunctional allyls and copolymers thereof. The spacer film may be clear, opaque or colored. The lamination of the film may be accomplished by using an adhesive, such as a pressure sensitive adhesive, a hot melt adhesive, a heat, moisture or radiation curable adhesive. Alternatively, the pre-punched spacer film may be laminated onto the substrate by heat or by using a suitable solvent for the spacer film, followed by drying. Examples of suitable solvents include THF, acetone, methylethylketone, cyclohexanone, ethyl acetate and derivatives thereof and these solvents are particularly useful for PMMA and polycarbonates. The substrate layer may optionally comprise an electrode layer.

There may be a primer layer (15) between the microcups and the substrate layer, which primer layer may be formed from a material such as polyacrylate, polyurethane, polyurea, polystyrene, polybutadiene, polyester, polyether, cellulose resins, phenolic resins, melamine formaldehyde resins or a combination thereof. The material for the primer layer may be the same as the material used for the formation of the microcups.

As stated above, the term "microcup" may also be referred to as "display cell". In general, the microcups can be of any shape, and their sizes and shapes may vary. The microcups may be of substantially uniform size and shape in one system. However, it is possible to have microcups of mixed shapes and sizes.

The openings of the microcups may be round, square, rectangular, hexagonal or any other shape. The size of the partition area between the openings may also vary.

The dimension of each individual microcup without sub relief structures may be in the range of about $1 \times 10^1$ to about $1 \times 10^6$ µm$^2$, preferably from about $1 \times 10^2$ to about $1 \times 10^6$ µm$^2$ and more preferably from about $1 \times 10^3$ to about $1 \times 10^5$ µm$^2$.

With the presence of the sub relief structures, the microcup may be in the range of about $1 \times 10^2$ to about $1 \times 10^8$ µm$^2$, more preferably from about $1 \times 10^3$ to about $10^7$ µm$^2$.

The depth of the microcups may be in the range of about 5 to about 200 microns, preferably from about 10 to about 100 microns. The opening to the total area ratio is in the range of from about 0.05 to about 0.95, preferably from about 0.4 to about 0.9.

2. Liquid Composition

The term "liquid composition", in the context of the present invention, refers to the composition which is filled in the microcups and is broadly defined as a substance that has the tendency to flow. It may be a solution, suspension/dispersion, emulsion, gel or the like. The liquid composition can be water based, organic based or silicone or fluorocarbon based.

The liquid composition filled into the microcups may be one single liquid composition or a mixture of two or more liquid compositions.

In addition, not all of the microcups have to be filled with the same liquid composition. For example, for display applications, the microcups may be filled with display fluids of different colors to generate different colors in different areas. As a result, a display device may have a certain number of microcups filled with a liquid composition of a first color, a certain number of microcups filled with a liquid composition of a second color and so on.

The filling of the liquid composition into the microcups may be accomplished by a conventional printing technique, such as inkjet, gravure, screen printing, spray printing or strip coating.

For pharmaceutical applications, different liquid compositions which are physically incompatible may be filled in different microcups. The ratio of the microcups filled with different liquid compositions may be pre-determined. For example, in a pharmaceutical device (i.e., a transdermal delivery system), some of the microcups may be filled with one liquid composition comprising a first active ingredient while other microcups may be filled with another liquid composition comprising a second active ingredient. The ratio of the two groups of microcups may be determined by the target doses of the two active ingredients. Such a feature is possible with the present invention because each microcup is a discreet and sealed unit, intermixing of different liquid compositions is not likely to occur.

It is noted that after being filled into the microcups, the liquid composition may change its physical state (i.e., turned into a solid, semi-solid or elastic state). A liquid crystal composition comprising a mixture of liquid crystals and a polymer precursor may also be polymerized and phase separated after being filled into the microcups There are a variety of liquid compositions suitable for the present invention.

A reverse emulsion electrophoretic display may be formed from the present film structure. A reverse emulsion comprises a mixture of a polar solvent (e.g., DMSO, DMF, dimethylacetamide, dimethyl sulfone, sulfonlane, hexamethylphosphoric triamide, higher amides, methanol, ethanol, glycols, nitromethane, acetonitrile, water, methoxyethanol, methyl cellosolve or monoethyl ethers) and a non-polar solvent (e.g., $C_{1-30}$ alkanes, $C_{2-30}$ alkenes, $C_{3-30}$ alkynes, $C_{3-30}$ aldehydes, $C_{3-30}$ ketones, $C_{2-30}$ ethers, $C_{3-30}$ esters, $C_{3-30}$ thioesters, $C_{3-30}$ thioethers, terpenes, $C_{2-30}$ organosilanes or $C_{2-30}$ organosiloxanes, each of which may be cyclic or acyclic and may be optionally substituted with halides or other non-polar substituents) and a hydrophilic dye. Suitable hydrophilic dyes may include, but are not limited to, cationic or anionic monoazo dyes, cationic or anionic diazo dyes, triphenylmethane dyes, pyrazolone dyes, acridines, charged porphyrines, oxazines, diformzans, colored metal and transition metal complexes, metal salts, acid anthraquinone dyes, amphoteric anthraquinone dyes, cationic diphenylmethane dyes, charged polymethine dyes, thiazines, charged phthalocyanines, formazans, and tetrazolium dyes. The solvent mixture may be stabilized with a surfactant and the dye may be present only in the non-continuous polar phase droplets. The droplets can be charged or can be otherwise responsive to an electric field. This property of the droplets is used to arrange the droplets within a pixel. The primary behavior of interest is that the droplets may spread out over the area of the pixel which results in a colored pixel or the droplets may be compacted which results in a transparent pixel.

Polymer dispersed liquid crystals (PDLC), reverse-mode PDLC, polymer network liquid crystals (PNLC), polymer encapsulated liquid crystals (PELC), ferroelectric liquid crystals, cholesteric liquid crystals or polymer stabilized cholesteric texture (PSCT) may also be used as the liquid composition.

A polymer dispersed liquid crystal (PDLC) display device usually has a higher polymer concentration (in the form of a polymer matrix) at about 20% to about 80% by weight and the liquid crystals dispersed randomly in the polymer matrix are in the form of micron-sized droplets. Such a PDLC film can be switched from a translucent state to a transparent state when the applied voltage exceeds a threshold.

For a composition of polymer network liquid crystals (PNLC) or polymer stabilized cholesteric texture, the polymer concentration is relatively low (e.g., below 30%) and the polymer in the composition forms a three-dimensional network to stabilize the liquid crystals or the cholesteric texture. These compositions are generally in a continuous state. The composition filled into the microcups is a homogeneous mixture of liquid crystals and a polymer precursor. As a three-dimensional polymer network is formed, by radiation or thermally, the liquid crystals and the polymer form two separate phases.

In the preparation of a polymer dispersed liquid crystal display device or polymer network liquid crystal display device utilizing the film structure, a precursor composition comprising liquid crystals and a polymer precursor in the state of an isotropic liquid is first filled into the microcups, followed by sealing the liquid composition within the microcups. After the filled microcups are sealed, the filled and sealed microcups are irradiated by a UV light to cause phase separation of a polymer formed from the polymer precursor, from the liquid crystals. Alternatively, the precursor composition may be first filled into the microcups, followed by radiation curing to form the PDLC or PNLC morphology and finally the sealing step. In the latter case, nitrogen blanket or Argon protection is preferably used during radiation curing of the liquid crystal composition to minimize the effect of oxygen inhibition.

The polymerization of the polymer precursor in either case may be achieved by radiation, thermally or other means, such as electron beams.

In the final product prepared from any of these methods, a liquid crystal composition comprising a polymer matrix or three-dimensional polymer network and liquid crystal droplets forms discrete units which are separated by microcup partition walls and enclosed in the individual microcups.

In the PDLC or PNLC liquid crystal display, the refractive indices of the microcups and the sealing layer preferably are matched to the refractive index of the liquid crystals.

Suitable polymer precursors in the precursor composition may include, but are not limited to, acrylates, methacrylates, thiols, alkenes, allyl ethers. Optionally, a photoinitiator of about 0.01 to about 5% may be present to trigger the polymerization. A photoinitiator is selected from the group consisting of benzoinether initiators, benzophenone-type initiators and thiozanthone-type initiators.

In the precursor composition, the weight ratio of the liquid crystals to the polymer precursor may range from about 1% to about 80%, preferably from about 2% to about 60%.

A composition of cholesteric liquid crystals comprising liquid crystals having positive dielectric anisotropy and a chiral material in an amount effective to form focal conic and twisted planar textures may also be used as the liquid composition. The chiral material has a pitch length effective to reflect light in the visible spectrum wherein the focal conic and twisted planar textures are stable in the absence of an electric field and the liquid crystals are capable of changing the textures upon application of an electric field. Suitable chiral materials for this composition may include, but are not limited to, CB15, CE2 and TM74A (manufactured by Merck). A polymer, such as UV curable thermoplastic and thermosetting polymers, may be further added to enhance the stability of the image, as in a polymer stabilized cholesteric texture. The chiral material needs to be selected, depending on the liquid crystals used, for optimal performance.

The composition of cholesteric liquid crystals may further comprise a polymer network. In addition, the inside surface of the microcups may be textured. It is also possible to have an alignment or anchoring layer fabricated on the inside surface of the microcups. The sealing layer may also serve as an alignment or anchoring layer.

The concentration of the chiral material may range from about 0.5% to about 30% if there is a polymer present in the composition or range from about 20% to about 70% if there is no polymer present in the composition.

The liquid composition may also be a display fluid as described in U.S. Pat. Nos. 4,126,854, 5,754,332, 6,497,942 and 6,588,131, the contents of all of which are incorporated herein by reference in their entirety. Briefly, the liquid composition of a so-called twisting ball display device may comprise millions of small beads randomly dispersed in a dielectric fluid. The beads, each contained in an oil-filled cavity, are free to rotate within those cavities. The beads are "bichromal" with hemispheres of two contrasting colors (e.g., black and white, red and white), and charged so they exhibit an electrical dipole. When a voltage is applied, the beads rotate to present one colored side to the viewer.

The liquid composition may be a nematic colloid. The nematic colloid may comprise nematic liquid crystals, nanoparticles of silica and/or clay. The regular nematic liquid crystals (positive dielectric anisotropy) usually switch in one direction under an applied voltage, from an initial scattered state to a homeotropic transparent state, which is stabilized by an internal volume nanoparticle network and retained after switching off the applied voltage.

The liquid composition may also be an electrophoretically controlled nematic liquid crystal composition. In this case, polarity controlled electromigration of the nanoparticles results in the stabilization of molecular alignment and provides bistable or multistable switching in a conventionally designed liquid crystal structure.

The liquid composition may also be a guest-host liquid crystal composition. Such a composition comprises nematic liquid crystals and dichroic dye(s). The dichroic dye absorbs a light component whose oscillation face is parallel to the major axis of the dichroic dye. In addition, a light component whose oscillation face perpendicular to the major axis of the dichroic dye is transmitted through the guest-host liquid-crystals. The nematic liquid crystals (host) and the dichroic dye (guest) are aligned homogeneously under no applied-voltage. Under an applied voltage, the nematic liquid-crystal molecules, as well as the dichroic dye, are aligned perpendicular to the direction of an electric field. Light can be modulated to be absorbed or transmitted through the guest-host liquid crystals, thus absorption contrast can be created.

The film structure may also be used for pharmaceutical applications, in particular as a transdermal delivery device (e.g., plaster or patch). Such a delivery device may be used for local or systemic drug delivery. The liquid composition, in this case, comprises an active ingredient which may be a medicinal or cosmetic agent. The medicinal agent may include substances intended for use in the diagnosis, cure, mitigation, treatment or prevention of diseases, or to affect the structure or function of the body. The medicinal agent may be a single chemical entity or a pharmaceutically acceptable salt thereof which will be present in an amount such that the device delivers a therapeutically effective amount for the indication being treated. The amount that constitutes a therapeutically effective amount will vary according to the type of the medicinal agent used, the condition to be treated, any medicinal agents being coadministered, the amount of time the composition is allowed to remain in contact with the skin of the patient, and other factors known to those of skill in the art.

The active ingredient present in the liquid composition will generally be about 0.01 to about 40% by weight, preferably about 1.0 to about 20% by weight, based on the total weight of the composition.

Any drug that is suitable for transdermal delivery can be used in the film structure of the present invention. Examples of useful drugs include, but are not limited to, anti-inflammatory drugs, antibacterials, antiprotozoals, antifungals, coronary vasodilators, calcium channel blockers, bronchodilators, enzyme inhibitors, antihypertensives, anti-ulceratives, steroidal hormones, antivirals, immunomodulators, local anesthetics, antitussives, antihistamines, narcotic analgesics, peptide hormones, sex hormones, enzymes, antinauseants, anticonvulsants, immunosuppressives, psychotherapeutics, sedatives, anticoagulants, analgesics, antiarrhythmics, antiemetics, contraceptives, anticancer agents, neurologic agents, hemostatics, anti-obesity agents, smoking cessation regimens or the like.

The most commonly used transdermal delivery systems include those having an active ingredient, such as nicotine for smoking cessation, or opioid medications for round-the-clock relief for severe pain, or hormones (such as estrogen for treatment of menopausal symptoms or postmenopausal osteoporosis, hormones for contraceptive, or testosterone), or nitroglycerin for treatment of angina, or scopolamine for treatment of motion sickness, or anti-hypertensive drug, or antidepressant, or medications for treatment of ADHD (attention deficit hyperactive disorder), or vitamins especially vitamin B12.

The liquid composition for pharmaceutical applications may also comprise excipients, such as a solvent, cosolvent, solubilizer, solvent modifier, permeation enhancer, preservative, buffering agent or the like. The solvent is the principal component of the liquid composition and preferably is one in which the active ingredient is soluble or at least substantially soluble or can be made soluble or become soluble, by addition of a co-solvent or solvent modifier. Suitable solvents may be selected from any of the solvents normally used for medicaments, cosmetics, nutrients or other active agents to be delivered transdermally. Preferred solvents include lower alcohols of from 2 to 6 carbon atoms, preferably from 2 to 4 carbon atoms and may be monoalcohols, such as, ethanol, isopropanol or sec-butanol, or polyols, such as, ethylene glycol, propylene glycol, butylene glycol or glycerol. A mixture of solvents may also be used. Other solvents, such as ketone (e.g., acetone or methylethyl ketone), ethers (e.g., ethylether) may also be used, in an amount which will be safe and non-toxic. While the solvent system is generally non-aqueous, water may be used for water soluble active ingredients and for those active ingredients which are stable in the presence of and not denigrated by the presence of water. When water is present in the solvent, in some cases, it will usually constitute less than about 50 percent, preferably less than about 10 percent, more preferably less than about 2 percent, by weight of the total solvent although more or less may be used, depending on the active ingredient and as long as the objective of the invention can be met.

Generally, the total amount of solvent(s) will be selected to assure dissolution of the active ingredient and excipients and provide suitable product viscosity. The amount of solvent(s) falling within the range of from about 5 to about 90 percent, preferably from about 25 to about 75 percent, based on the total composition, may be used.

The liquid composition preferably is in the form of a solution. However it is also possible to be in form of a suspension/dispersion, emulsion, gel or the like.

3. Sealing of the Filled Microcups

The sealing of the filled microcups may be accomplished in a number of ways. Because the top-openings of the filled microcups are sealed, the sealing may also be referred to as "top-sealing".

One approach is to disperse a sealing composition in the liquid composition. The sealing composition is immiscible with the liquid composition and preferably has a specific gravity lower than that of the liquid composition. The two compositions, the sealing compositing and the liquid composition, are thoroughly mixed and immediately coated onto the microcups with a precision coating mechanism such as Myrad bar, gravure, doctor blade, slot coating or slit coating. Excess fluid is scraped away by a wiper blade or a similar device. A small amount of a weak solvent or solvent mixture such as isopropanol, methanol or an aqueous solution thereof may be used to clean the residual fluid on the top surface of the partition walls of the microcups. The sealing composition subsequently separates from the liquid composition and floats on top of the liquid composition.

Alternatively, after the mixture of the liquid composition and the sealing composition is filled into the microcups, a substrate may be laminated on top to control the metering of the mixture of compositions and to facilitate the phase separation of the sealing composition from the liquid composition to form a uniform sealing layer. The substrate used can be a functional substrate in the final structure or can be a sacrifice substrate, for example, a release substrate, which can be removed afterwards.

A sealing layer is then formed by hardening the sealing composition in situ (i.e., when in contact with the liquid composition). The hardening of the sealing composition may be accomplished by UV or other forms of radiation such as visible light, IR or electron beam. Alternatively, heat or moisture may also be employed to harden the sealing composition if a heat or moisture curable sealing composition is used.

Alternatively, the liquid composition may be filled into the microcups first and a sealing composition is subsequently overcoated onto the filled microcups. The overcoating may be accomplished by a conventional coating and printing process, such as blanket coating, inkjet printing or other printing processes. A sealing layer, in this approach, is formed in situ, by hardening the sealing composition by solvent evaporation, radiation, heat, moisture, or an interfacial reaction. Interfacial polymerization followed by UV curing is very beneficial to the sealing process. Intermixing between the liquid composition and the sealing overcoat is significantly suppressed by the formation of a thin barrier layer at the interface by interfacial polymerization and the sealing is then completed by a post curing step, preferably by UV radiation. To further reduce the degree of intermixing, the specific gravity of the sealing composition preferably is lower than that of the liquid composition. Volatile organic solvents may be used to adjust the viscosity and thickness of the sealing overcoat. Rheology of the sealing composition may be adjusted for optimal sealability and coatability. When a volatile solvent is used in the overcoat, it is preferred that it is immiscible with the solvent in the liquid composition.

The components in the sealing composition are very much dependent on the chemical and physical nature of the liquid composition. Preferably, the sealing composition and its solvent have a solubility of less than about 10%, preferably less than about 5% and more preferably less than about 3%, in the liquid composition or vise versa. However, even if the solubility is higher than 10%, there are approaches to adjust the rheology, for example, viscosity and elasticity, surface tension or interfacial tension, to avoid intermixing.

In general, the sealing material in the sealing composition may be a thermoplastic, thermoset or precursor thereof. Examples of such materials may include, but are not limited to, polyvalent acrylate or methacrylate, cyanoacrylate, polyvalent vinyl including vinylbenzene, vinylsilane, vinylether, polyvalent epoxide, polyvalent isocyanate, polyvalent allyl, oligomers or polymers containing crosslinkable functional groups and the like.

Surfactants may also be added to the sealing composition to improve the adhesion and wetting at the interface between the liquid composition and the sealing layer. Useful surfactants include both ionic and non-ionic surfactants, These surfactants may include, but are not limited to, FC surfactants (from 3M Company), Zonyl fluorosurfactants (from DuPont) and BYK surfactants (from BYK Chemie USA, Inc.), polysiloxane based surfactants (e.g., Silwet and Silquest surfactants from OSI Specialties, Inc.), block copolymers of ethylene and propylene oxide, alkylaryl polyethers (e.g., ethoxylation products of lauryl, oleyl, stearyl alcohols and ethoxylated nonylbenzene), alkali metal or ammonium salts of fatty acids; alkyl, aryl or alkyl aryl sulfonates, sulfates, phosphates and mixtures thereof.

Other additives may also be added to the sealing composition to assist in the film formation, to improve sealing stability or to provide other functions necessary for the processing of the final product. Examples of suitable additives may include polymeric binder or thickener, photoinitiator, catalyst, filler, colorant, surfactant, plasticizer, antioxidant or organic solvents. The additive may also be a rheology modifier such as the associative thickener ACRYSOL (from Rohm and Haas Co.), CAB-O-SIL fumed silica (from Cabot Corp.) or photostabilizers such as ultraviolet light stabilizers commercially available under the trade designation TINUVIN from Ciba. Sealing precursors or additives may exist as an emulsion or dispersion in the sealing composition.

Other suitable sealing compositions are disclosed in U.S. Pat. No. 7,005,468, U.S. patent application Ser. No. 10/665,898 (Publication No. 2004-0120024A), Ser. No. 10/651,540 (Publication No. 2004-0112525A) and Ser. No. 10/762,196 (Publication No. 2004-0219306A), the contents of all of which are incorporated herein by reference in their entirety.

As the liquid composition can be water based, organic based, silicone or fluorocarbon based. The components in the sealing composition may be selected accordingly.

For the water based liquid composition, the sealing material in the sealing composition may be a hydrophobic organic polymer, such as polyacylate, polyvinyl ether, polyvinyl acetal, polycarbonate, polystyrene, polyurethane, polyurea, polyester, polyethylene, polypropylene, poly(isoprene), polybutadiene, vegetable, mineral wax, polycarprolactone, polyorthoester, polyanhydride, epoxy resin, alkyd resin, polyvinyl chloride, a cellulose derivative or a copolymer thereof. It is also possible to use a silicone polymer or a fluorinated polymer, such as polymers with PDMS (polydimethylsilane) sub-units, polymers with perfluocarbon sub-units, polymers with perfluoroether sub-units or copolymers thereof. Monomers or oligomers of similar chemical nature may be present in the sealing composition for further curing of the sealing composition. The solvent used in such type of sealing composition may be an organic solvent, such as alkanes, ketones, ethers, alcohols or a halogenated solvent, such as FC-43 (primarily $C_{12}$ perfluorinated compounds from 3M), a halocarbon oil (from Halocarbon Products Corporation), a Galden fluid (low molecular weight perfluoropolyethers from Solvay), a low molecular weight Krytox fluid (perfluoroalkylethers from DuPont) or a PDMS containing solvent, depending on the solubility of the sealing material used in the composition.

For the organic based liquid composition, the sealing material may be a water soluble polymer with water as the sealing solvent. Examples of suitable water soluble polymers or water soluble polymer precursors may include, but are not limited to, polyvinyl alcohol; polyethylene glycol, its copolymers with polypropylene glycol, and its derivatives, such as PEG-PPG-PEG, PPG-PEG, PPG-PEG-PPG; poly(vinylpyrolidone) and its copolymers such as poly(vinylpyrrolidone)/vinyl acetate (PVP/VA); polysaccharides such as cellulose and its derivatives, poly(glucosamine), dextran, guar gum, and starch; gelatin; melamine-formaldehyde; poly(acrylic acid), its salt forms, and its copolymers; poly(methacrylic acid), its salt forms, and its copolymers; poly(maleic acid), its salt forms, and its copolymers; poly(2-dimethylaminoethyl methacrylate); poly(2-ethyl-2-oxazoline); poly(2-vinylpyridine); poly(allylamine); polyacrylamide; polyethylenimine; polymethacrylamide; poly(sodium styrene sulfonate); cationic polymer functionalized with quaternary ammonium groups, such as poly(2-methacryloxyethyltrimethylammonium bromide), poly(allylamine hydrochloride). The sealing material may also include a water dispersible polymer with water as a formulating solvent. Examples of suitable polymer water dispersions may include polyurethane water dispersion and latex water dispersion. Suitable latexes in the water dispersion include polyacrylate, polyvinyl acetate and its copolymers such as ethylene vinyl acetate, and polystyrene copolymers such as polystyrene butadiene and polystyrene/acrylate.

In one embodiment, the sealing composition comprises (i) a water soluble polymer as described above, (ii) a water-based suspension, a water-based dispersion, a water-based emulsion, or a water-based latex, each comprising an epoxy resin or a polymer selected from the group consisting of polyurethane, polyacrylate, polyvinyl acetate, polyvinyl chloride, polystyrene, and the copolymer thereof; and (iii) water; wherein the top-sealing layer is on top of, and in contact with, the electrophoretic fluid. The sealing composition may further comprise a fourth component, i.e., a water soluble or water dispersable UV curable monomer, oligomer, or polymer such as ethoxylated or propoxylated mono, bi, tri, or multifunctional acrylate; ethoxylated or propoxylated mono, bi, tri, or multifunctional methacrylate; or polymers comprising segments that facilitate the water comparability such as polyethylene glycol or polar groups, e.g., hydroxyl, aimine, acid, etc. Alternatively, the sealing composition may comprise a different fourth component, i.e., a water soluble or water dispersable thermal crosslinker, coupling agent, or adhesion promoter; such as polyisocyanate, blocked or encapsulated isocyanate, multifounctional polycarbodiimide, multifunctional aziridine, silane coupling agent, epoxy silane, boron/titanium/zirconium based crosslinker, Melamine formaldehydes It is also possible to use, as a sealing material, a silicone polymer or a fluorinated polymer. Such polymers may be selected from polymers that consist of PDMS sub-units or polymers with perfluorocarbon sub-units, polymers with perfluoroether sub-units or copolymers thereof. Monomers or oligomers of similar chemical nature may be present in the sealing composition for further curing of the composition. Suitable solvents may include solvents such as FC-43, halocarbon oil, a Galden fluid, a low molecular weight Krytox fluid or a PDMS containing solvent.

It is also possible to find incompatible organic polymers for certain organic based liquid composition, as the sealing material. If the organic solvent based liquid composition is hydrophilic, it may contain a significant amount of polymer groups, such as polyethylene oxide, alcohol or nitrile. In this case, the sealing material may be a hydrophobic polymer, such as polyisoprene, polyethylene, polypropylene, polybutadiene, copolymers thereof or the like and the solvent in the sealing composition may be a hydrophobic solvent, such as alkanes.

For a silicon and fluorocarbon based liquid composition, the sealing material may be a water soluble polymer with water as the sealing solvent in the sealing composition. Examples of suitable water soluble polymers may include, but are not limited to, cellulose polymers, latexes, pseudolatexes, gelatin, polyvinyl alcohol, polyethylene glycol, PEG-PPG-PEG, PPG-PEG, PPG-PEG-PPG, polyvinyl pyrolidone, PVP/VA polysaccharides, starch, melamine-formaldehyde, phospholipids and the like. The sealing material may also be a hydrophobic organic polymer, such as poly(acrylate), polycarbonate, polystyrene, polyurethane, polyethylene, polypropylene, poly(isoprene), polybutadiene, vegetable, mineral wax, polycarprolactone, polyorthoester, polyanhydride, epoxy or copolymer thereof. Monomers or oligomers of similar chemical nature may be present in the sealing composition for further curing of the sealing composition. The solvent used in the sealing composition may also be an organic solvent, such as alkanes, ketones, ethers, alcohols or the like.

The sealing layer is one of the critical features of the film structure of the present invention. The sealing composition can be formulated to achieve certain desired chemical or physical properties of the final product. For example, for display applications, the sealing layer, when properly formulated, can cut down the voltage drop in order to increase the effective voltage applied to the display panel.

The sealing layer may also be modified beyond meeting the requirements of coatability and sealability on the filled microcups. For example, the sealing layer may contain a photo-alignment composition, which upon radiation will create an alignment surface in contact with the composition filled in the microcups.

For transdermal delivery applications, the active ingredient permeates through the sealing layer at a desired rate. Diffusion of the active ingredient through the sealing layer is dependent on properties of the active ingredient, the solvent in which the active ingredient is present, the chemical nature of the sealing layer/adhesive layer or any other layers in between the active ingredient and the skin. The rate of diffusion, in general, tends to decrease with increased molecular volume. The rate of skin penetration, on the other hand, is a function of the diffusion coefficient, the barrier partitioning tendency, binding affinity and the rate of metabolism of the active ingredient by the skin. The sealing layer, in this aspect of the invention, is preferably a continuous or microporous film. A continuous film may be prepared from, for example, ethylene:vinyl acetate copolymers which may contain an appropriate amount of vinyl acetate, for example, about 0.5 to about 40% by weight.

II. Display Device

The film structure (10) of FIG. 1 may be used in a display device. Examples of the liquid composition suitable for display devices are discussed in Section I.2. FIGS. 4A-4C depict various possible configurations of a display device.

In FIG. 4A, the film structure (40) is sandwiched between two electrode layers (41a and 41b). For illustration purpose, the side marked 40a is the sealing layer side. There may be a primer layer (42) between the film structure (40) and one of the electrode layers (41a). The primer layer may be formed from a material such as polyacrylate, polyurethane, polyurea, polystyrene, polybutadiene, polyester, polyether, cellulose resins, phenolic resins, melamine formaldehyde resins or a combination thereof. The material for the primer layer may be the same as the material used for the formation of the microcups. The microcups (44) are filled with a display fluid (i.e., a liquid composition 45) and sealed with a sealing layer (46). There may also be an adhesive layer (43) between the sealing side of the film structure and one of the electrode layers 41b. The display device as depicted may be viewed from the sealing side (if the sealing layer, the adhesive layer if present and the electrode layer 41b are transparent) or from the non-sealing side (if the primer layer if present and the electrode layer 41a are transparent).

For an in-plane switching mode display device such as the one disclosed in U.S. Pat. No. 6,885,495, the content of which is incorporated herein by reference in its entirety, the film structure is sandwiched between one substrate layer and one electrode layer.

For a display device, one side of the film structure may be a common electrode layer and the other side of the film structure may be applied by a writing pen or a scanning device with a voltage on its bare surface to achieve image updating.

FIGS. 4B and 4C depict display panels which are referred to as a semi-finished display panel.

In FIG. 4B, the semi-finished display panel comprises the film structure (40) sandwiched between a temporary substrate (47a) and an electrode layer or a permanent substrate layer (47b). The positions of the temporary substrate (47a) and the electrode or permanent substrate layer (47b) may be switched.

In FIG. 4C, the film structure (40) is sandwiched between two temporary substrate layers (48a and 48b).

The display panel or semi-finished display panel may be coated with a protective layer. The protective layer may be formed from silicone, a fluorocarbon compound, polyethylene or polypropylene, and is readily peeled off.

The primer (42) and adhesive (43) layers may be also optionally present in any of the semi-finished display panels as exemplified.

The semi-finished display panels may be formed by any of the methods disclosed in this application and U.S. patent application Ser. No. 10/351,460 (Publication No. 2003-0179436A), the content of which is incorporated herein by reference in its entirety.

The temporary substrate such as a release liner may be formed from a material selected from the group consisting of polyethylene terephthalate (PET), polycarbonate, polyethylene (PE), polypropylene (PP), paper and a laminated or cladding film thereof. A silicone release coating may also be applied onto the temporary substrate to improve the release properties.

The temporary substrate layer may comprise a conductive layer coated on either side of the temporary substrate layer or the temporary substrate layer may be conductive itself.

The semi-finished display panel may be supplied to customers in the form of a roll and the customers may cut the roll of the semi-finished panel into desired formats and sizes to meet their specific needs.

The conversion of a semi-finished panel to a finished display panel is exemplified in FIGS. 5A-5D.

FIG. 5A depicts a roll of semi-finished display panel. FIG. 5B depicts a cross-sectional view of a semi-finished display panel comprising a film structure (50) sandwiched between a temporary substrate (51) and a first electrode layer or a permanent substrate layer (52). The side marked 50a is the sealing layer side. The temporary substrate (51) is laminated over the film structure, optionally with an adhesive layer (53a) between the film (50) and the temporary substrate (51). The layer 53 is a sealing layer. FIG. 5C depicts that the temporary substrate (51) is peeled off. In FIG. 5D, a second electrode layer (54) is laminated onto the film structure. Alternatively, the electrode layer may be disposed onto the film structure by a method such as coating, printing, vapor deposition, sputtering or a combination thereof.

In the finished display panel shown in FIG. 5D, either the sealing side 50a or the non-sealing side may be the viewing side.

When the semi-finished panel comprises a film structure is sandwiched between two temporary substrate layers, the semi-finished display panel may be converted to a finished display panel by removing the two temporary substrate layers, followed by laminating two permanent substrate layers, at least one of which comprises an electrode layer, over the film structure. Alternatively, the permanent substrate layers may be disposed onto the film structure by a method such as coating, printing, vapor deposition, sputtering or a combination thereof.

For display applications, any layer in the path of the electrical field may be further optimized according to the driving method to maximize the effective driving voltage on the display medium. For example, for DC driven displays, layers in the path of the electrical field preferably have relative low electrical resistance as compared to that of the active display medium. Low electrical resistance may be achieved by controlling the $T_g$, polarity and the crosslinking density of the polymer matrix of the layer(s), or by adding conductive fillers or fillers of low resistance to the layer(s). For AC driven displays, these layers prefer to have high dielectric constant. High dielectric constant may be achieved by addition of fillers of high dielectric constant, for example, Perovskite, barium titanate (BaTiO) or lead titanate (PbTiO3). For current driven displays, these layers prefer to be conductive. Conductivity may be achieved by using conductive polymers or addition of conductive fillers.

Figure 9:
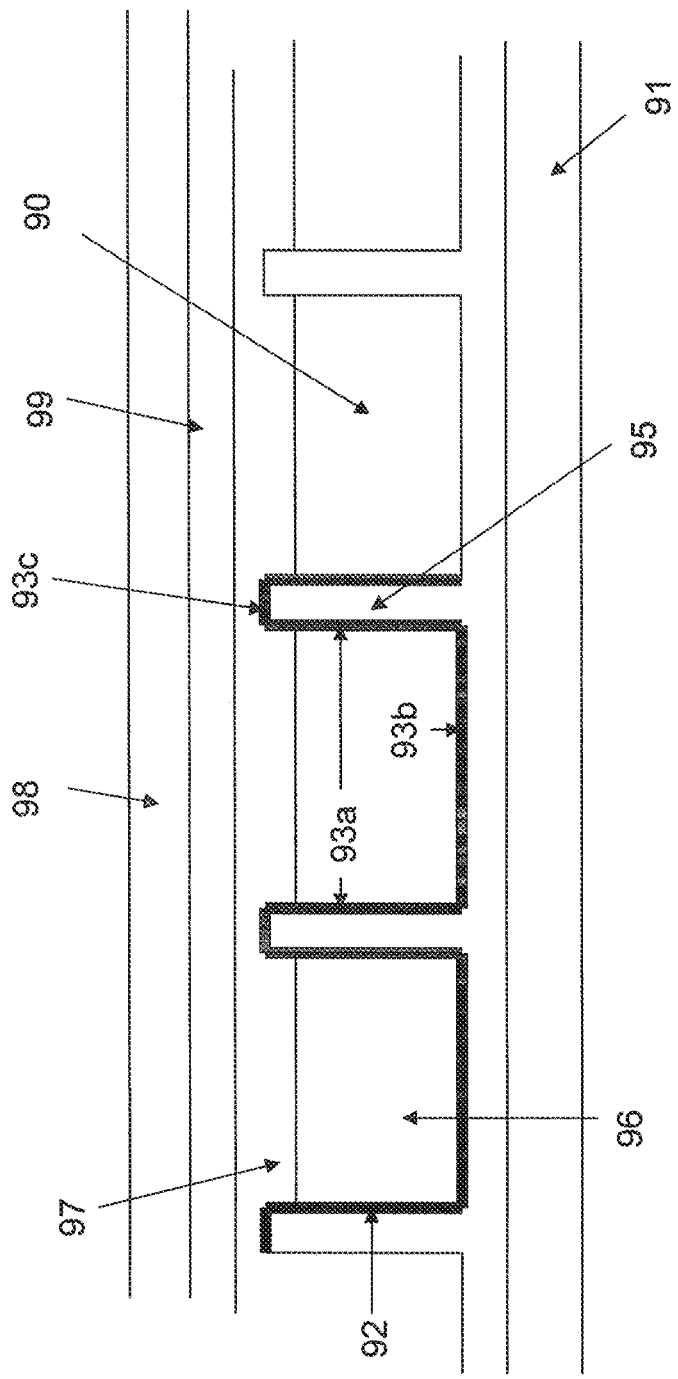
FIG. 9 illustrates a display device in which the inside surface of the display cells (e.g., microcups) are coated with a conductive layer.

FIG. 9 illustrates a display device prepared by an alternative process. In this process, a film structure comprising microcups (90) is formed directly on a first substrate (91). Useful non-conducting substrates may include, but are not limited to, glass, metal sheets or films overcoated or laminated with a non-conducting or dielectric layer, and plastic films such as epoxy resins, polyimide, polysulfone, polyaryl-ether, polycarbonate (PC), polyethylene terephthalate (PET), polyethylene terenaphthalate (PEN), poly(cyclic olefin) and composites thereof.

The microcups may be formed by any of the methods as described in this application. After the formation of the microcups, a first conductive layer (92) is formed on the surface (93) of the microcups which includes the side surface (93a), the bottom surface (93b) and the top surface (93c) of the partition walls (95). In one embodiment, the first conductive layer may be formed on only the side surface (93a) and the bottom surface (93b). In another embodiment, the first conductive layer may be formed on the side surface (93a), bottom surface (93b) and the top surface (93c) of the partition walls and in this case the first conductive layer on the top surface (93c) of the partition walls may be later removed completely or partially. The first conductive layer is of a discrete pattern when the conductive layer on the top surface of the partition walls is completely removed. In this case, the discrete first conductive layers may be connected to the driving components through via holes.

The first conductive layer may be formed on the surface of the microcups by electroless plating, sputtering, vacuum deposition, printing, or a combination thereof. Useful conductive layers may include, but are not limited to, metal conductors such as aluminum, copper, zinc, tin, molybdenum, nickel, chromium, silver, gold, iron, indium, thallium, titanium, tantalum, tungsten, rhodium, palladium, platinum or cobalt, and the like, and metal oxide conductors such as indium tin oxide (ITO) or indium zinc oxide (IZO), as well as alloys or multilayer composite films derived from the aforementioned metals and/or metal oxides, or conductive polymers. Further, the conductive layer described herein may comprise either a single layer thin film or a multilayer thin film. ITO films are of particularly interest in many applications because of their high degree of transmission in the visible light region.

The patterning of the first conductive layer may be accomplished by, for example, a photolithographic process which comprises steps including (i) coating the conductor film with a photoresist, (ii) patterning the photoresist by imagewise exposing it through a photomask to, for example, ultraviolet light, (iii) "developing" the patterned image by removing the photoresist from either the exposed or the unexposed areas, depending on the type of photoresist used, to uncover the conductive layer in areas from which it is to be removed (i.e., areas where no electrode lines are to be located), (iv) using a chemical etching process to remove the conductive layer from the areas from which the photoresist has been removed and (v) stripping the remaining photoresist to uncover the electrode lines.

Alternatively, the photoresist may be printed onto the first conductive layer followed by etching and stripping to reveal the conductive pattern.

Still alternatively, the conductive layer may be patterned by dry etching using laser or by laminating an adhesive tape on the microcup surface and peeling off the conductive layer on selective areas of the surface.

Still alternatively, the first conductive layer may be patterned by printing a masking layer on the microcup surface followed by depositing a conductive layer by, for example, vapor deposition or sputtering. More specifically, the formation of the first conducting film on the microcup surface may be accomplished by first printing on the surface a strippable printing material. The printed strippable material defines an area on the surface where the conductive film structure is not to be formed. In other words, the printed strippable material is substantially not present in the area on the surface where the conductive film structure is to be formed. A thin layer of a conductive material is then deposited on the patterned surface, followed by stripping the strippable material from the surface, whereby the strippable material and any conductive material formed thereon are removed, leaving behind a patterned conductive film structure.

Alternatively, the formation of a patterned conductive film structure on the microcup surface may be accomplished by first printing a printable material on the surface that defines an area where the conductive film structure is to be formed. A conductive thin film is then deposited on the microcup surface. In this case, the conductive film adheres more strongly to the printable material than to the surface without the printable material. After stripping off the conductive film formed directly on the surface using a stripping process that does not strip the conductive film from the printable material, the conductive film structure remains formed on the printable material used to define the area in which the conductive film structure is to be formed. These methods are disclosed in a co-pending application, U.S. Ser. No. 10/422,557 filed Apr. 23, 2003 (corresponding to WO03/091788), the content of which is incorporated herein by reference in its entirety.

The first conductive layer deposited, particularly that on the top surface of the partition walls, may be selectively removed or patterned by, for example, (1) photolithographic exposure followed by etching and stripping, (2) laser dry etching or (3) laminating the conductive layer/microcup/substrate structure with an adhesive tape followed by mechanically peeling off the conductive layer on the top surface of partition walls.

After the first conductive layer is formed on the surface of the microcups, the microcups may then be filled with a display fluid (96) and sealed with a sealing layer (97) as described in sections above. Optionally, an electrode protective layer may be coated onto the first conductive layer before the filling and sealing of the display fluid.

If needed, the film structure comprising filled and sealed microcup is then laminated with a second conductive layer (98) optionally with an adhesive layer (99). If the second conductive layer is deposited by, for example, thin film sputtering or vapor deposition, a second non-conducting substrate layer may be laminated onto the second conductive layer, optionally with an adhesive layer.

The first conductive layer (92) has a thickness in the range of 1 nm to 3000 nm, preferably in the range of 20 nm to 500 nm, more preferably in the range of 50 nm to 150 nm.

There may be a third conductive layer (not shown) between the film structure comprising microcups (90) and the first substrate (91), particularly when a discrete conductor pattern is formed on the film structure. The first conductive layer may be of a discrete pattern (i.e., not connected) by, for example, removing the conductive layer on the top surface of the partition walls.

The second and third conductive layers independently may also be patterned by any of the methods described above.

In one embodiment, the first conductive layer may be disposed onto the surface of the microcups by thin film deposition (e.g., sputtering or vapor deposition). In another embodiment, the second conductive layer may be formed on the film structure by thin film deposition, printing or lamination. In a further embodiment, the third conductive layer, if present, may be formed on the first substrate by thin film deposition, printing or lamination and the microcups are formed on the third conductive layer.

This display fluid (96) referred to in this aspect of the invention may be any of the liquid composition/display fluid mentioned above. For example, the display fluid may be a liquid crystal composition comprising liquid crystals and a polymer matrix or a three-dimensional polymer network; or a liquid crystal composition comprising liquid crystals and a chiral material.

III. Transdermal Delivery Device

The film structure (10) of FIG. 1 may be used in a transdermal delivery film. Examples of the liquid composition suitable for transdermal delivery devices are discussed in Section I.2. The formation of a sealing layer which may serve as a diffusion membrane of the delivery system is discussed in Section I.3.

Figure 8:
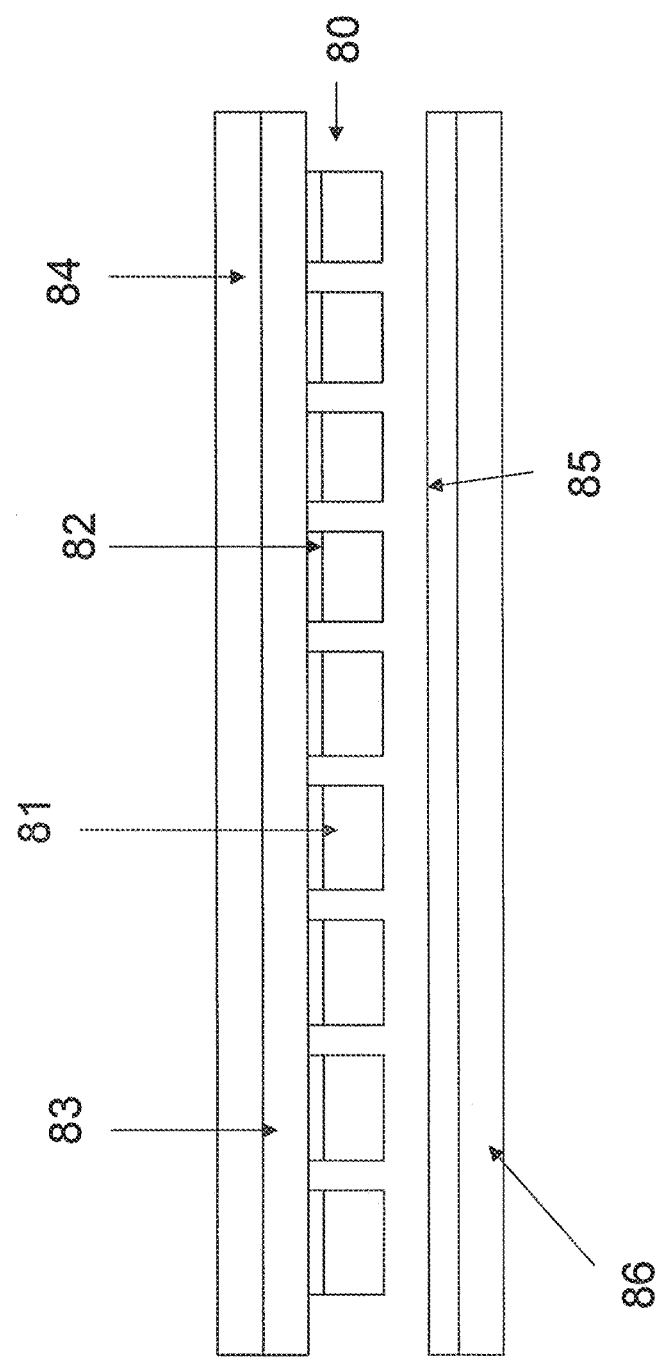
FIG. 8 depicts an example of a transdermal delivery film.

FIG. 8 depicts an example of a transdermal delivery system of the present invention. The film structure (80) comprises one or more microcups which are filled with a liquid composition (81) containing an active ingredient. Each of the microcups is sealed with a sealing layer/diffusion membrane (82). There is a skin contact layer (83) which has some adhesion property to allow the film structure to be adhered to the skin of a patient. Any pressure sensitive adhesive layer is suitable as the skin contact layer. The skin contact layer preferably has good permeability to water vapor (i.e., perspiration) and air. Suitable skin contact pressure sensitive adhesives may include, but are not limited to, acrylate copolymers, synthetic rubbers, such as polyisobutylenes, polyisoprenes, styrenes block copolymers, polyvinylethers, silicone polymers and a combination thereof.

A release liner (84) is placed over the skin contact layer (83). The release liner that can be peeled away before use so that the drug-containing film structure may be exposed. The release layer may be formed from a polymer known in the art which is either peelable by nature or from a polymer which is rendered impermeable to the active ingredient by treating the surface with silicone or a fluorocarbon compound which is readily stripped off. The microcups are formed on a substrate layer (86). There may also be an optional primer layer (85).

The thickness (excluding the substrate thickness) of the transdermal delivery film is generally in the range of about 5 μm to about 500 μm, preferably from about 10 μm to about 200 μm.

IV. Preparation of Film Structure Containing One Single Liquid Composition

Figure 6:
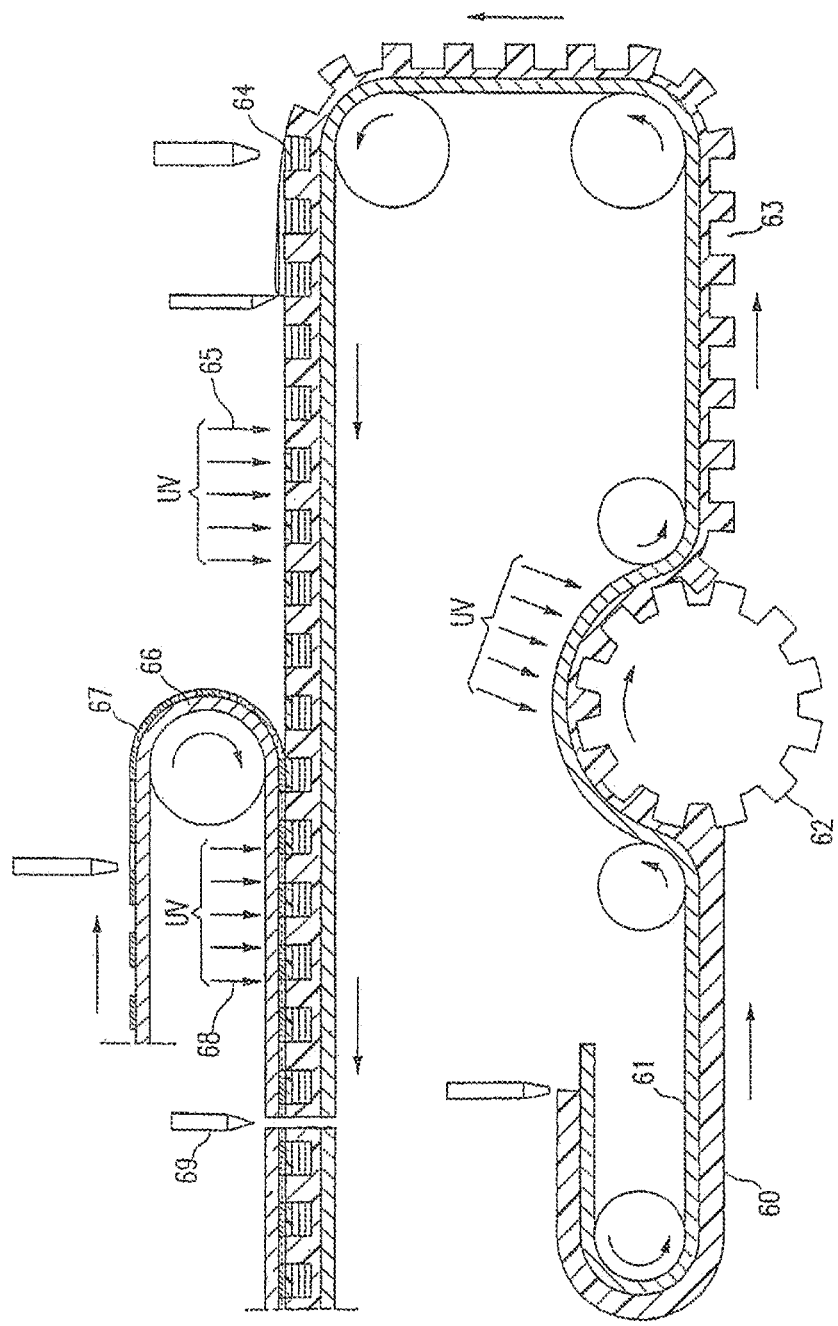
FIG. 6 illustrates a process involving a film structure containing one single liquid composition.
Figure 7A:
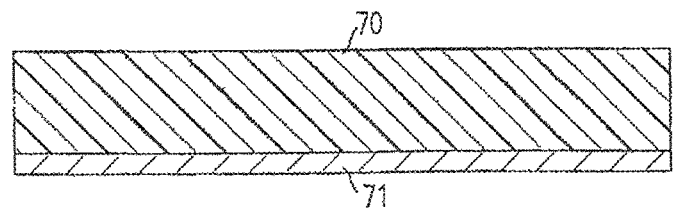
FIGS. 7A-7H illustrate a process involving a film structure containing more than one liquid composition.
Figure 7B:
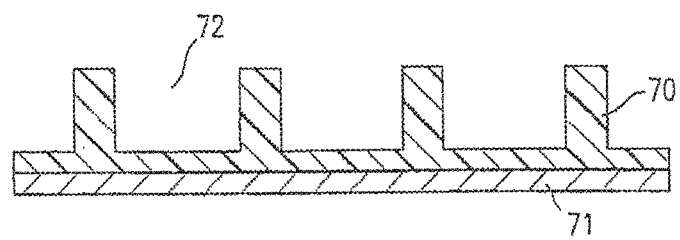
Figure 7C:
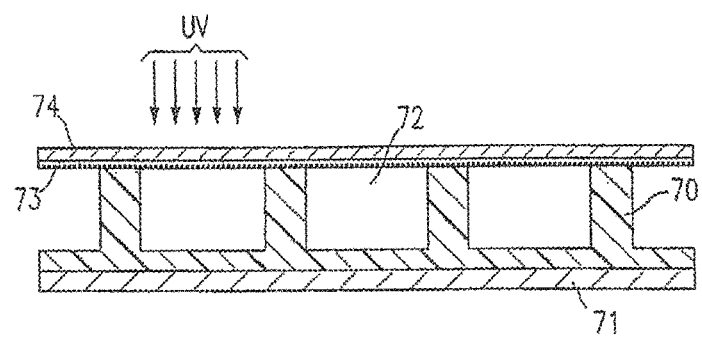
Figure 7D:
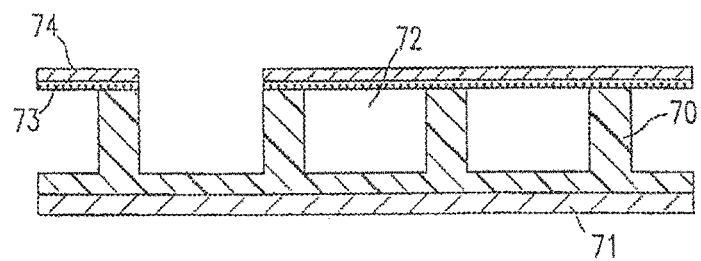
Figure 7E:
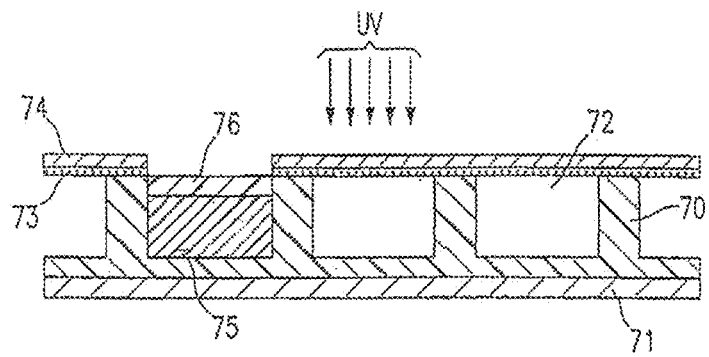
Figure 7F:
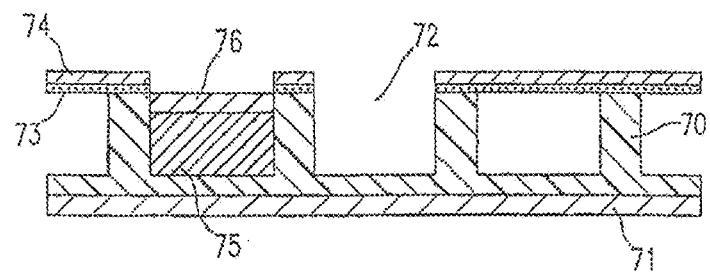
Figure 7G:
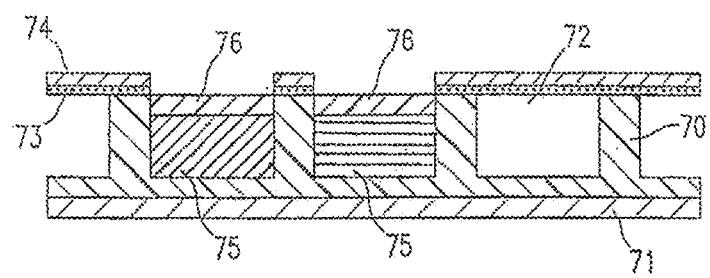
Figure 7H:
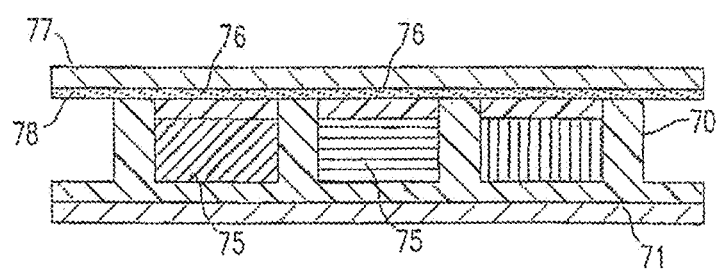

The process is illustrated by the flow diagram as shown in FIG. 6. All microcups are filled with the same liquid composition. The process can be a continuous roll-to-roll process comprising the following steps:

1. Coat a layer of an embossable composition (60) on a substrate layer (61). The substrate layer may comprise an electrode layer, depending on the intended final product.
2. Emboss the embossable composition at a temperature higher than the glass transition temperature of the embossable composition by a pre-patterned male mold (62).
3. Release the mold from the embossable composition layer preferably during or after the layer is hardened.
4. Fill in the thus-formed microcups (63) with a liquid composition (64).
5. Seal the filled microcups by one of the sealing methods (e.g., UV curing 65) discussed in Section I.3.
6. Laminate other layers (e.g., 66) over the filled and sealed microcups as needed. An adhesive (67) may be used for the lamination step. The adhesive may be a pressure sensitive adhesive, a hot melt adhesive, a heat, moisture or radiation curable adhesive. The laminate adhesive may be post cured by radiation such as UV (68). The finished film containing the film structure may then be cut (69) to desired dimensions after the lamination step.

In Step 6, an electrode layer, instead of being laminated onto the film structure, may be directly formed on the film structure by a method such as coating, printing, vapor deposition, sputtering or a combination thereof. An active matrix driving structure may also be directly built on the film structure.

The preparation of the microcups described above can be conveniently replaced by the other methods disclosed in Section I.1.

V. Preparation of Film Structure Containing More Than One Type of Liquid Compositions For the manufacture of a film structure containing more than one type of liquid compositions, additional steps are needed. These additional steps include (1) laminating the already formed microcups with a positively working dry-film photoresist; (2) selectively opening a pre-determined amount of the microcups by imagewise exposing the photoresist; (3) filling the opened microcups with a first liquid composition; and (4) sealing the filled microcups by one of the methods discussed in Section I.3. These additional steps may be repeated to create microcups filled with liquid compositions of different types.

For display applications, the different liquid compositions may contribute to different colors or other switching properties. For transdermal delivery systems, the different liquid compositions may have different active ingredients or different compositions containing the same active ingredient. These are only a few examples.

More specifically, a film structure containing different types of liquid compositions may be prepared according to the steps as shown in FIGS. 7A-7H.

1. Coat a layer of an embossable composition (70) on a substrate layer (71). The substrate layer may comprise an electrode layer, depending on the intended final product.
2. Emboss the embossable composition layer at a temperature higher than the glass transition temperature of the embossable composition by a pre-patterned male mold.
3. Release the mold from the embossable composition layer preferably during or after the embossable composition is hardened.
4. Laminate the thus formed microcups (72) with a positive dry-film photoresist (74) and an adhesive layer (73).
5. Imagewise expose (FIG. 7C) the positive photoresist by UV, visible light, or other radiation means to open microcups in the exposed area. The purpose of Steps 4 and 5 is to selectively open the microcups in a predetermined area (FIG. 7D).
6. Fill the opened microcups with a first liquid composition (75).
7. Seal the filled microcups (76) by any one of the sealing methods discussed is Section I.3.
8. Steps 5-7 described above may be repeated to generate microcups filled with different liquid compositions in different areas (FIGS. 7E, 7F and 7G).
9. Laminate the filled and sealed microcups with other layers (77) if needed. The lamination may be accomplished optionally with an adhesive (78), such as a pressure sensitive adhesive, a hot melt adhesive, a heat, moisture or radiation curable adhesive.
10. Harden the adhesive, if necessary.

In Step 9, instead of lamination, an electrode layer may be directly disposed onto the film structure by a method such as coating, printing, vapor deposition, sputtering or a combination thereof. An active matrix driving structure may also be directly built on the film structure.

The filling of the microcups may also be accomplished by metering in different liquid compositions at predetermined locations by inkjet printing. Alternatively, the different components in the liquid composition can be dissolved in a volatile solvent, and inkjet printed first. After drying, the common liquid compositions may be blanket coated, followed by sealing.

The preparation of the microcups described in the process above may conveniently be replaced by the alternative methods discussed in Section I.1.

The thickness of the film structure of the present invention can be as thin as a piece of paper. The width of the film structure is the width of the coating web (typically 3-90 inches). The length of the film structure may be anywhere from inches to thousands of feet depending on the size of the roll.

The film structure may be incorporated into a device. It is understood that a device may have one or more layers of the film structure.

One of the key advantages of the present invention is that the film structure may be manufactured roll-to-roll on a web continuously or semi-continuously.

A continuous process is demonstrated in FIG. 6 where the embossing and filling/sealing are carried out continuously without interruption. A semi-continuous process is a process in which some of the steps may be carried out continuously; but not the entire process. For example, there may be an interruption between the formation of the microcups and the filling/sealing steps or there may be an interruption between the filling/sealing steps and the lamination step.

The process as shown in FIGS. 7A-7H may also be carried out continuously or semi-continuously. In other words, the multiple steps may be carried out continuously without interruption or some of the steps may be carried out continuously but not the entire process.

Furthermore, in either a continuous process or a semi-continuous process, one or more of the steps may be carried out in a stop-n-go fashion. The stop-n-go mode may be carried out at regular or irregular intervals.

The film structure of the present invention enables such format flexible and efficient roll-to-roll continuous or semi-continuous manufacturing. These processes are easily scalable, can be carried out efficiently, at low cost.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, materials, compositions, processes, process step or steps, to the objective and scope of the present invention. All such modifications are intended to be within the scope of the claims appended hereto.

The invention claimed is:

1. A flexible controlled-release film for delivering a medicinal or cosmetic agent, consisting of:
   a) a continuous flexible acrylate film embossed to create a plurality of microcells, each microcell having a floor, walls, and a top opening;
   b) a liquid composition disposed in the microcells, the liquid composition comprising a medicinal or cosmetic agent;
   c) a continuous flexible semi-porous sealing layer disposed over the top openings of the plurality of microcells, the continuous flexible semi-porous sealing layer holding the liquid composition within the plurality of microcells;
   d) an adhesive skin contact layer adjacent the continuous flexible semi-porous sealing layer; and
   e) a release layer adjacent to the adhesive skin contact layer.

2. The flexible controlled-release film of claim 1, wherein said microcells are filled with more than one type of liquid composition comprising medicinal or cosmetic agents.

3. The flexible controlled-release film of claim 2, wherein a first plurality of microcells are filled with a first type of liquid composition comprising medicinal or cosmetic agents and a second plurality of microcells are filled with a second type of liquid composition comprising medicinal or cosmetic agents.

4. The flexible controlled-release film of claim 1, wherein said medicinal or cosmetic agent is in an amount of about 0.01 to about 40% by weight based on the total weight of the liquid composition.

5. The flexible controlled-release film of claim 1, wherein the medicinal or cosmetic agent diffuses across the continuous flexible semi-porous sealing layer.

6. The flexible controlled-release film of claim 1, wherein the continuous flexible semi-porous sealing layer comprises a polyacrylate, a polyvinyl ether, or a polyvinyl acetate.

7. The flexible controlled-release film of claim 1, wherein the continuous flexible semi-porous sealing layer comprises a polyvinyl alcohol, a polyethylene glycol, or a polypropylene glycol.

8. The flexible controlled-release film of claim 1, wherein the flexible controlled-release film is between 10 μm and 200 μm in thickness.

* * * * *